(12) United States Patent
Müller

(10) Patent No.: US 8,088,814 B2
(45) Date of Patent: Jan. 3, 2012

(54) METHODS AND COMPOSITIONS FOR THE TREATMENT OF PSYCHIATRIC DISORDERS

(76) Inventor: Norbert Müller, München (DE)

( * ) Notice: Subject to any disclaimer, the term of this patent is extended or adjusted under 35 U.S.C. 154(b) by 1299 days.

(21) Appl. No.: 10/157,969

(22) Filed: May 31, 2002

(65) Prior Publication Data

US 2003/0130334 A1  Jul. 10, 2003

Related U.S. Application Data

(60) Provisional application No. 60/364,904, filed on Mar. 14, 2002.

(30) Foreign Application Priority Data

Jun. 19, 2001  (DE) .................. 101 29 320

(51) Int. Cl.
*A61K 31/365* (2006.01)
*A61K 31/415* (2006.01)
*A61K 31/353* (2006.01)

(52) U.S. Cl. ......... 514/406; 514/456; 514/471; 514/602

(58) Field of Classification Search .................. 514/456, 514/406, 471, 602
See application file for complete search history.

(56) References Cited

U.S. PATENT DOCUMENTS

| | | | |
|---|---|---|---|
| 5,466,823 A | 11/1995 | Talley et al. | |
| 5,633,272 A | 5/1997 | Talley et al. | |
| 5,639,441 A * | 6/1997 | Sievers et al. | 424/9.3 |
| 5,663,194 A * | 9/1997 | Mewshaw | 514/456 |
| 5,760,068 A | 6/1998 | Talley et al. | |
| 5,840,924 A | 11/1998 | Desmond et al. | |
| 5,932,598 A | 8/1999 | Talley et al. | |
| 5,945,539 A | 8/1999 | Haruta et al. | |
| 5,981,576 A | 11/1999 | Belley et al. | |
| 5,994,381 A | 11/1999 | Haruta et al. | |
| 6,001,843 A | 12/1999 | Dube et al. | |
| 6,002,014 A | 12/1999 | Haruta et al. | |
| 6,004,948 A | 12/1999 | Blaschke et al. | |
| 6,020,343 A | 2/2000 | Belley et al. | |
| 6,034,256 A | 3/2000 | Carter et al. | |
| 6,046,236 A | 4/2000 | Hamanaka et al. | |
| 6,057,319 A | 5/2000 | Black et al. | |
| 6,071,936 A | 6/2000 | Dube et al. | |
| 6,071,954 A | 6/2000 | LeBlanc et al. | |
| 6,077,850 A | 6/2000 | Carter et al. | |
| 6,077,869 A | 6/2000 | Sui et al. | |
| 6,083,969 A | 7/2000 | Ferro et al. | |
| 6,127,545 A | 10/2000 | Pye et al. | |
| 6,133,292 A | 10/2000 | Wang et al. | |
| 6,140,515 A | 10/2000 | Chen et al. | |
| 6,169,188 B1 | 1/2001 | Belley et al. | |
| 6,180,651 B1 | 1/2001 | Nicolai et al. | |
| 6,204,387 B1 | 3/2001 | Davies et al. | |
| 6,222,048 B1 | 4/2001 | Black et al. | |
| 6,239,173 B1 | 5/2001 | Wang et al. | |
| 6,291,523 B1 | 9/2001 | Fujimoto et al. | |
| 6,297,282 B1 | 10/2001 | Hartmann et al. | |
| 6,300,363 B1 | 10/2001 | Stevens et al. | |
| 6,303,628 B1 | 10/2001 | Nakao et al. | |
| 6,306,890 B1 | 10/2001 | Kalgutkar et al. | |
| 6,307,047 B1 | 10/2001 | Black et al. | |
| 6,310,079 B1 | 10/2001 | Okumura et al. | |
| 6,310,099 B1 | 10/2001 | Fujimoto et al. | |

FOREIGN PATENT DOCUMENTS

| | | |
|---|---|---|
| EP | 0 196 132 | 1/1986 |
| JP | 2004-537514 | 12/2004 |
| WO | WO 98/03484 | 1/1998 |
| WO | WO 99/11605 | 3/1999 |
| WO | WO 99/25353 A1 * | 5/1999 |
| WO | WO 00/24719 | 5/2000 |
| WO | WO 00/25779 | 5/2000 |
| WO | WO 00/32189 | 6/2000 |
| WO | WO 02/089787 A1 | 11/2002 |

OTHER PUBLICATIONS

Das et al. Increased arachidonic acid induced platelet chemiluminescence indicates cycloxygenase overactivity in schizophrenic subjects. Prostaglandins Leukotrienes and Essential Fatty Acids, Mar. 1998 vol. 58, No. 3, pp. 165-168.*
Yolken RH, Torrey EF: "Viruses, schizophrenia, and bipolar disorder". Clin Microbiol Rev 1995; 8:131-145.
Körschenhausen D., Hampel H., Ackenheil M., Penning R., Müller N.; "Fibrin degradation products in post mortem brain tissue of schizophrenics: a possible marker for underlying inflammatory processes", Schizophr Res 1996; 19: 103-109.
Müller N., Ackenheil M., Psychoneuroimmunology and the cytokine-network in the CNS: implications for psychiatric disorders, Prog Neuropsychopharmacol & Biol Psychiat 1998; 22:1-33.
Sirota P., Schild K., Elizur A., Djaldetti M., Fishman P., "Increased Interleukin-1 and Interleukin-3 like activity in schizophrenic patients", Prog Neuropsychopharmacol & Biol Psychiatry 1995: 19: 83-85.
Licinio J., Seibyl JP., Altemus M., Charney DS., Krystal JH., Elevated levels of Interleukin-2 in Increases in neuroleptic-free schizophrenics. Am J Psychiatry 1993: 150: 1408-1410.
McAllister CG, van Kamen DP, Rehn TJ, Miller AL, Gurklis J, Kelley ME, Yao J, Peters JL: Increases in CSF levels of Interleukin-2 in schizophrenia: effects of recurrence of psychosis and medication status. Am J Psychiatry 1995: 152: 1291-1297.
Schwarz MJ, Riedel M, Ackenheil M, Müller N: "Decreased levels of soluble intercellular adhesion molecule-1 ($_S$ICAM-1) in unmedicated and medicated schizophrenic patients"., Biol Bsychiatry 2000; 47: 29-33.

(Continued)

*Primary Examiner* — Jennifer M Kim
(74) *Attorney, Agent, or Firm* — Crowell & Moring LLP

(57) ABSTRACT

A method for the prevention, treatment, or inhibition of a psychiatric disorder, in particular schizophrenia, is described which comprises administering a COX-2 inhibitor or prodrug thereof to a subject. Moreover, a method for the prevention, treatment, or inhibition of a psychiatric disorder, in particular schizophrenia or depressive disorders, is disclosed comprising administering to a subject a COX-2 inhibitor or prodrug thereof in combination with a neuroleptic drug or an antidepressant. Compositions and kits that are suitable for the practice of the method are also described.

21 Claims, 5 Drawing Sheets

OTHER PUBLICATIONS

Rapaport MH, Müller N: "Immounological states associated with schizophrenia", In: Ader R, Felten DL, Cohen N (eds) Psychoneuroimmunology, Third Edition. vol. 2, San Diego Academic Press, 2002; pp. 373-382.

Rapaport MH, McAllister CG, Kim YS, Han JH, Pickar D, Nelson DM, Kirch DG, Paul SM: "Increased soluble Interleukin-2 receptors in Caucasian and Korean schizophrenic patients", Bio Psychiatry 1994; 35: 767-771.

Kilidireas K, Latov N, Strauss DH, Aviva DG, Hashim GA, Gorman JM, Sadiq SA: "Antibodies to human 60 KD hear-shock protein in patients with schizophrenia"., Lancet 1992; 340: 569-572.

Schwarz MJ, Riedel M, Gruber R, Ackenheil M, Müller N: Antibodies to heat-shock proteins in schizophrenic patients—Implications for disease mechanism. Am J Psychiatry 1999: 156, 1103, 1104.

Schwarz MJ, Riedel M, Gruber R, Ackenheil M, Müller N: "Levels of soluble adhesion molecules in schizophrenia": Relation to psychopathology. In: N. Müller (Hrg) Psychiatry, Psychoneuroimmunology, and Viruses., Springer Verlad Wioen, 1999; NY, pp. 121-130.

Müller N, Ackenhiel M: Immunoglobulin and albumin contents of cerebrospinal fluid in schizophrenic patients: The relationship to negative sympomatology. Schizophrenia Res 1995; 14: 223-228.

Neeldeman, P., et al., J Rheumatol., 24, Suppl. 49: 6-8 (1997).

Fu, J.Y., et al., J. Biol. Chem., 265(28): 16737-40 (1990).

Samad, T.A. et al, Nature, 410(6827): 471-5 (2001).

Yoshimi, N. et al., in Japanese J. Cancer Res., 90(4): 406-412 (1999).

Iwata, K. et al., in Japan, J. Pharmacol., 75(2): 191-194 (1997).

Kirchner et al., in J Pharmacol Exp Ther 282, 1094-1101 (1997).

Goodman & Goldman's The Pharmacological Basis of Therapeutics, Ninth Edition (1996), Appendix II, pp. 1707-1711.

Müller N. Dobmeier P. Empel M, Riedel M, Shcwarz M, Ackenheil M: Soluble IL-6 Receptors in the serum and cerebrospinal fluid of paranoid schizophrenic patients. Eur Psychiatry 1997; 12: 294-299.

van Kammen DP, McAllister-Sistilli CG, Kelley ME: Relationship between immune and behavioral measures in schizophrenia . In: G. Wieselmann (ed.) Current Update in Psychoimmunology, Springer Verlad 1997; Wien, NY, pp. 51-55.

Schwarz MJ, Ackenheil M, Riedel M, Müller N: Blood-CSF-Barrier impariment as indicator for an immune process in shcizophrenia. Neurosci Letters 1998; 253: 201-203.

Stahl SM; Dopamine-system stabilizers, aripiprazole and the next generation of antipsychotics, partl, "goldilocks"—actions at dopamine receptors; j. Clin. Psychiatry 2001, 62, 11: 841-842.

American Psychiatric Associateion (1994), Diagnostic and Statistical Manual of Mental Disorders, $1^{st}$ Edition, American Psychiatric Press, Washington DC.

Kay et al., Schizophr. Bul. 1987, 13: 261-276.

Simpson and Angus, Acta Psychiat. Scand. 1970 (Suppl.), 212.

Schwieler et al., "Prostaglandin-mediated control of rat brain kynurenic acid synthesis—opposite actions COX-1 and COX-2 isoforms," *Journal of Neural Transmission*, 2004, Austria*.

Philippe Chavatte et al., "A Computational View of COX-2 Inhibition", Anti-Cancer Agents in Medicinal Chemistry, vol. 6, pp. 239-249, 2006.

C. Michaux et al., "Structural Approach for COX-2 Inhibition", Mini-Reviews in Medicinal Chemistry, vol. 4, pp. 603-615, 2004.

Robert Soliva et al., "Theoretical Studies on the Inhibition Mechanism of Cyclooxygenase-2. Is There a Unique Recognition Site?", J. Med. Chem., vol. 46, pp. 1372-1382, 2003.

Mewshaw et al., "New Generation Dopaminergic Agents. 1. Discovery of a Novel Scaffold Which Embraces the $D_2$ Agonist Pharmacophore. Structure-Activity Relationships of a Series of 2-(Aminomethyl)chromans", J. Med. Chem., (1997), vol. 40, pp. 4235-4256.

Schaad, et al., "Prostanoids and Their Role in Cell-Cell Interactions in the Central Nervous System", Neurohem Int. vol. 18, No. 3, pp. 303-322, 1991.

* cited by examiner

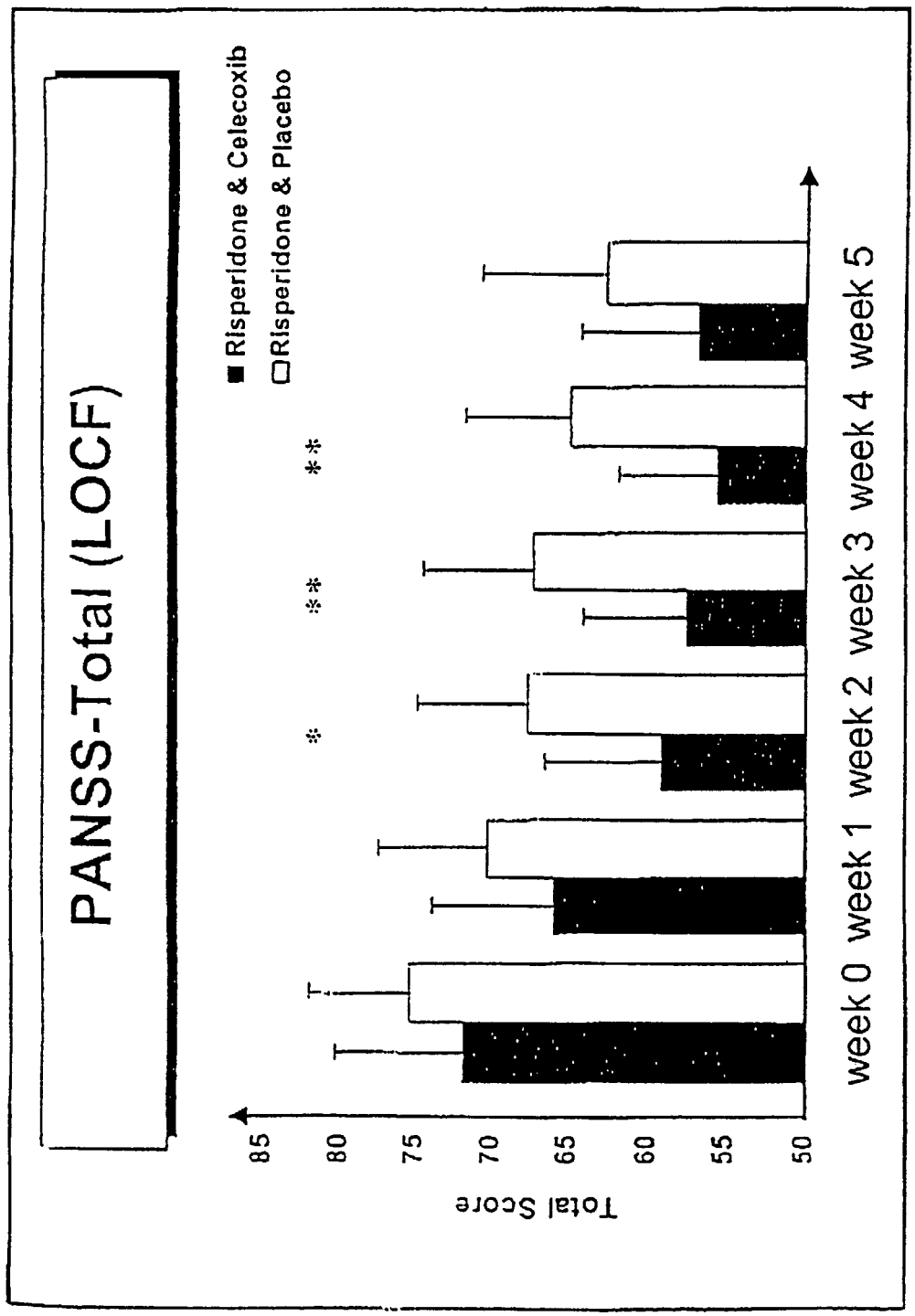
Figure 1: Comparison of the Panss total score during the treatment course of risperidone and celecoxib or risperidone and placebo

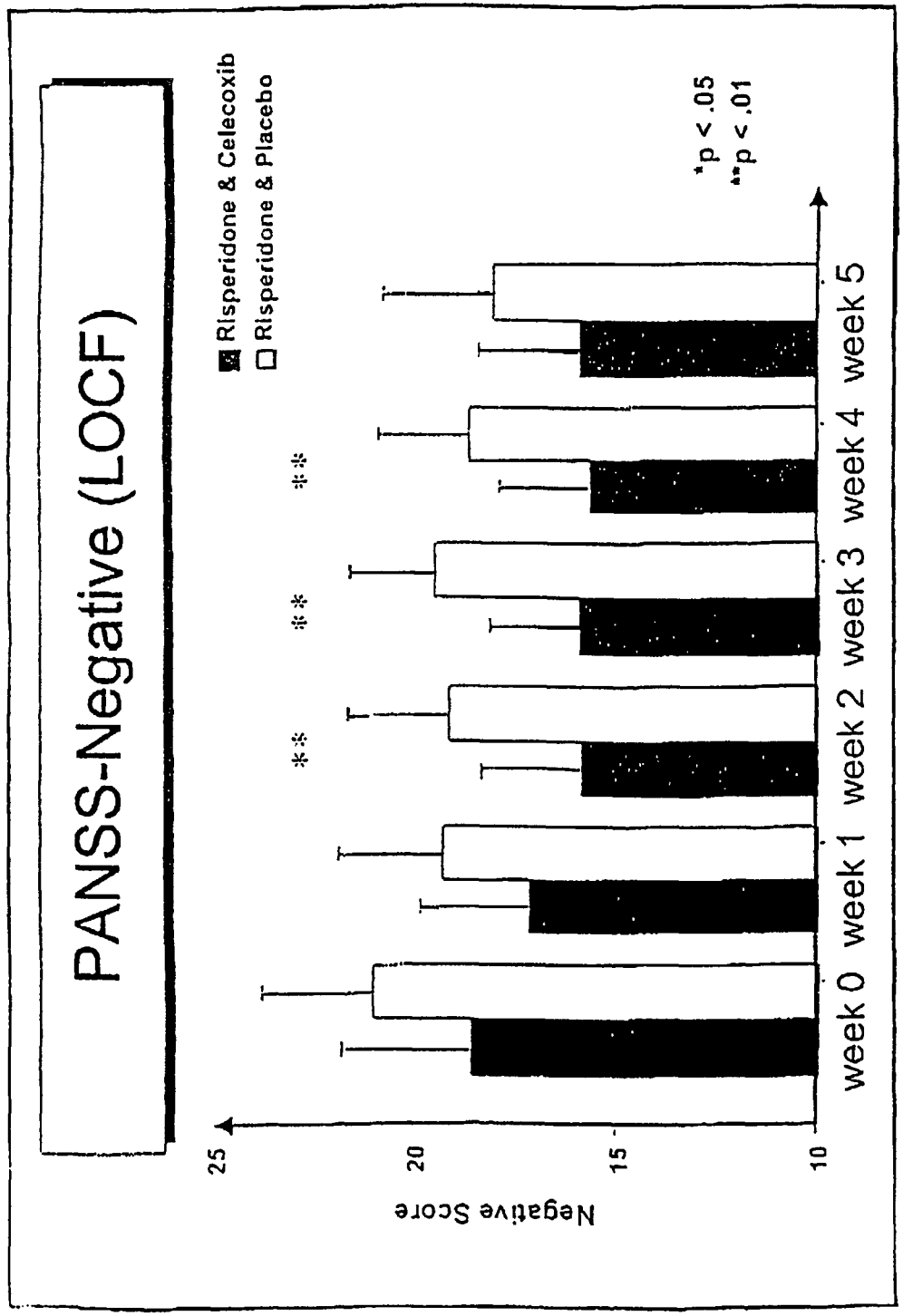
Figure 2: Comparison of the Panss negative score during the treatment course of risperidone and celecoxib or risperidone and placebo

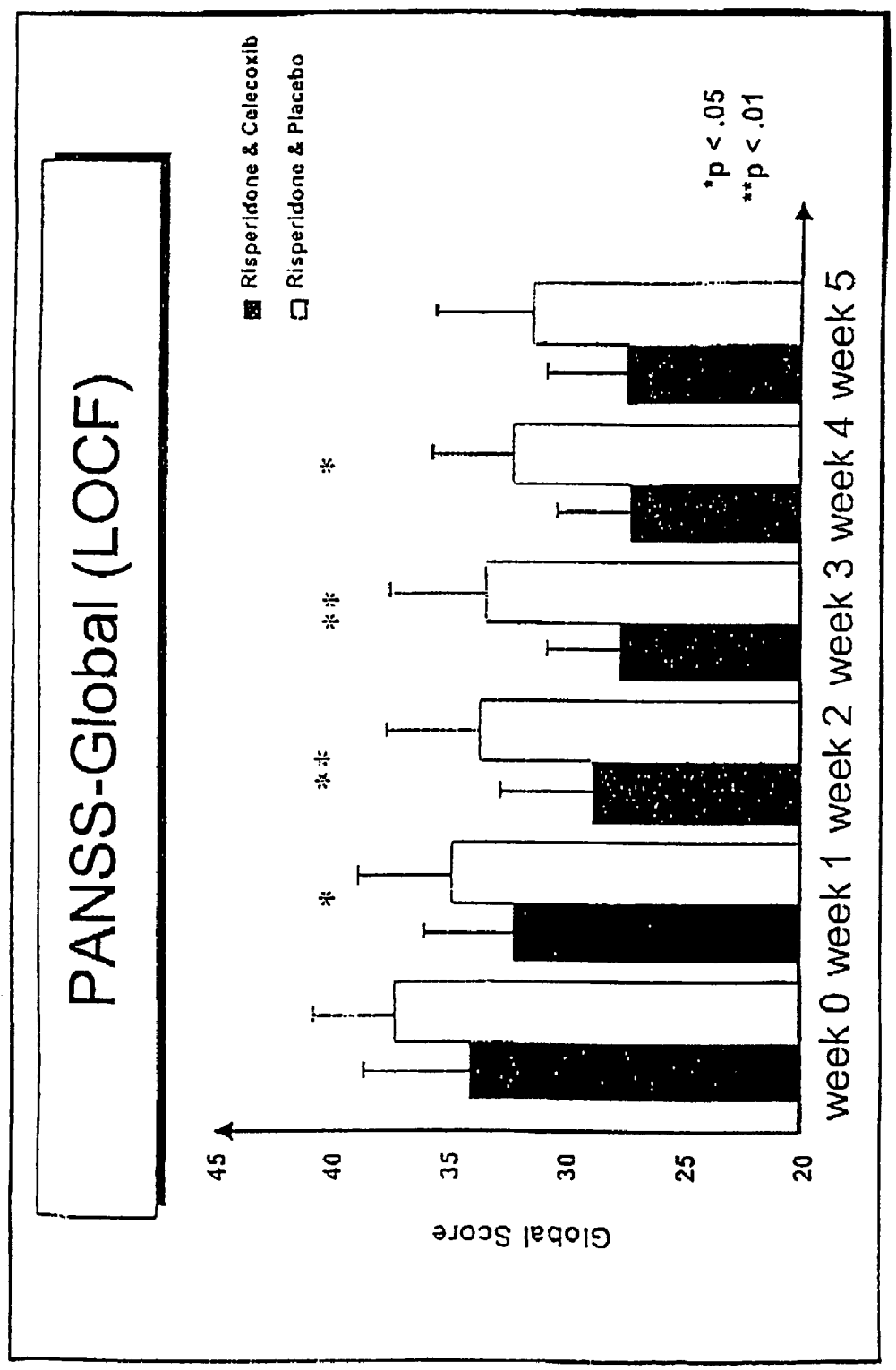
Figure 3: Comparison of the Panss global score during the treatment course of risperidone and celecoxib or risperidone and placebo

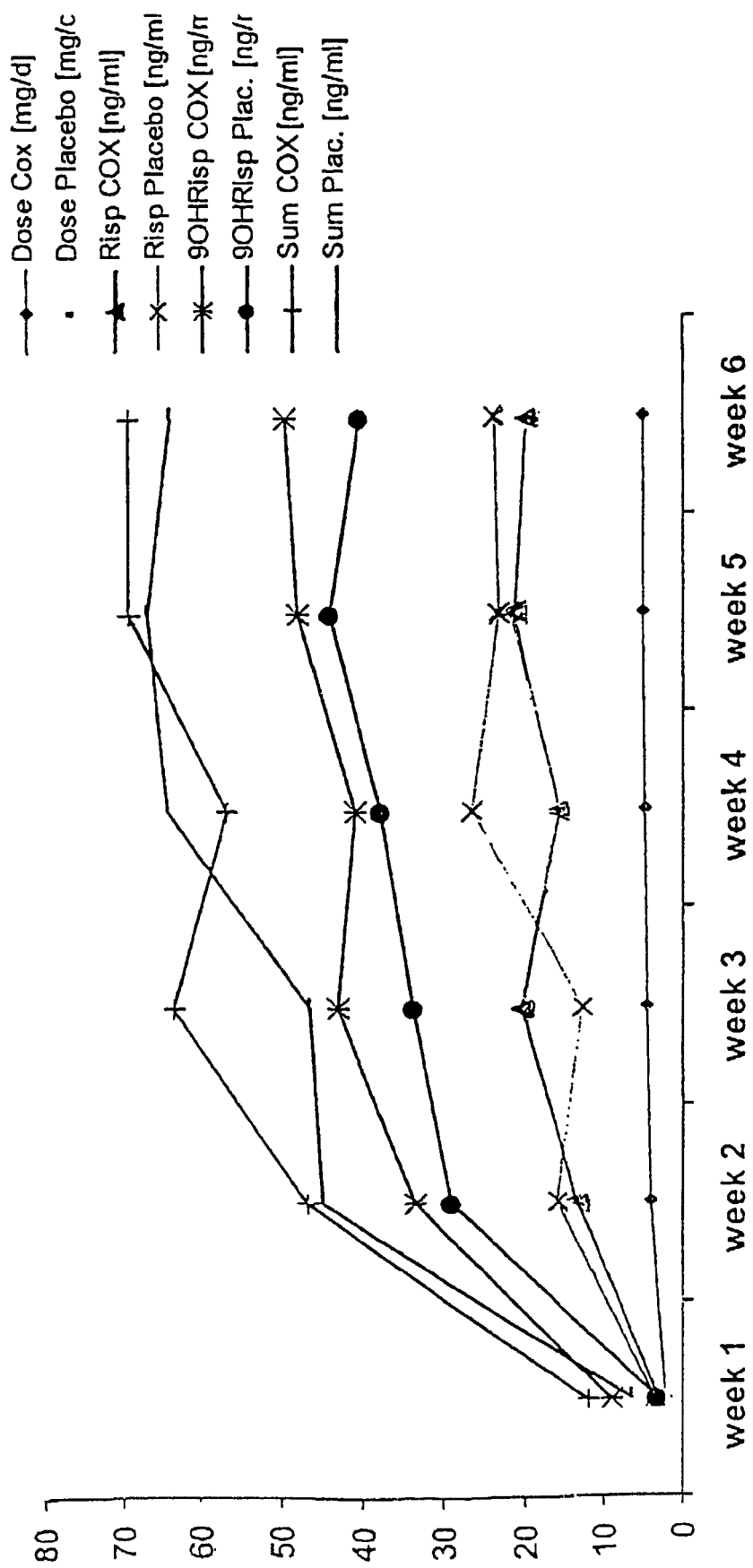
Figure 4: Plasma levels of Risperidone and 9OH-Risperidone during Celecoxib add-on and Placebo

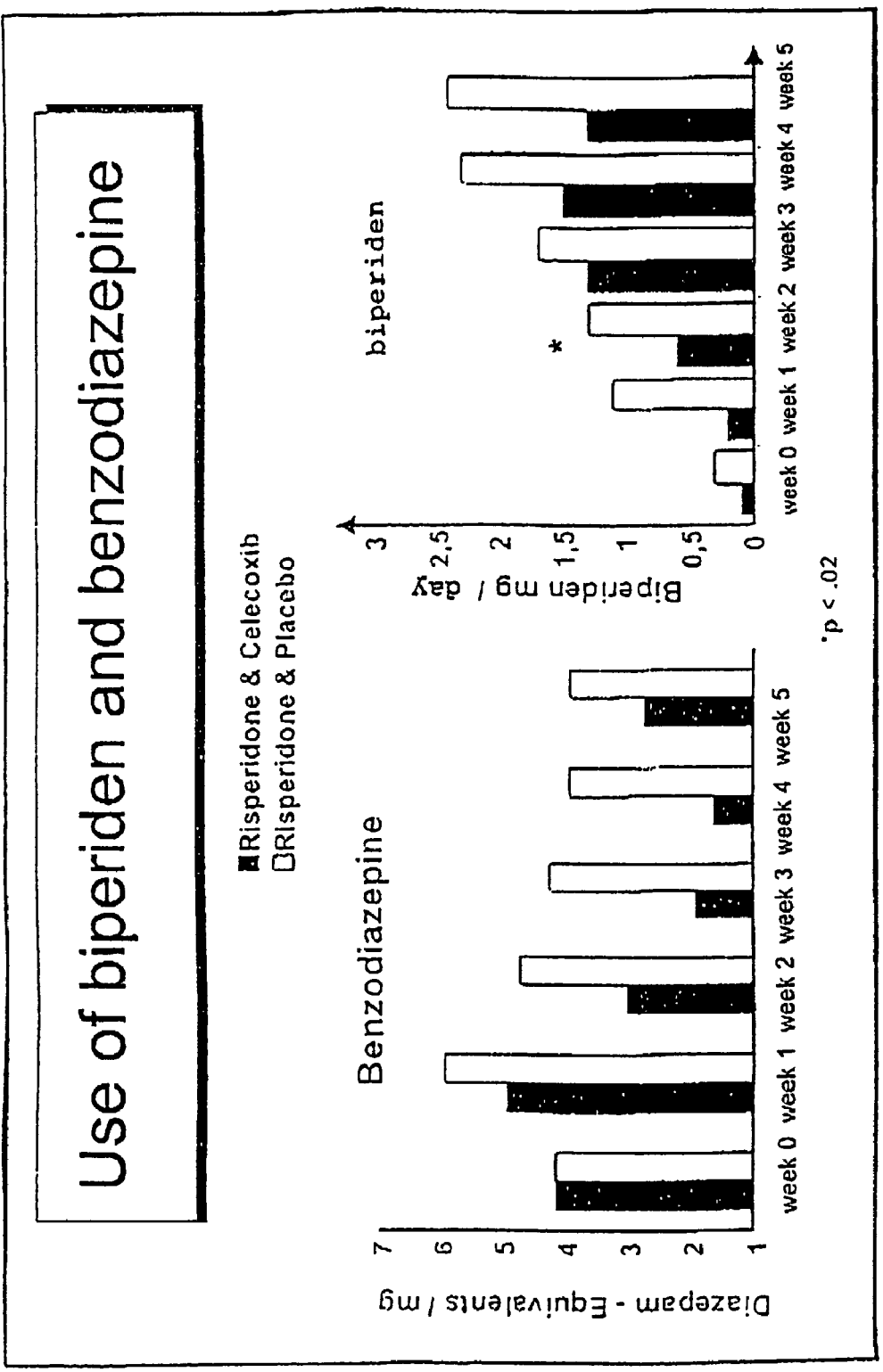
Figure 5: Use of biperiden and benzodiazepines during the Treatment with risperidone-celecoxib or risperidone-placebo

METHODS AND COMPOSITIONS FOR THE TREATMENT OF PSYCHIATRIC DISORDERS

This application claims priority under 35 U.S.C. §119 to U.S. Provisional Application No. 60/364,904 entitled and filed on 14 Mar. 2002, the entire content of which is hereby incorporated by reference.

BACKGROUND OF THE INVENTION

(1) Field of the Invention

The invention concerns a method for treating psychiatric disorders such as schizophrenia, delusional disorders, affective disorders, autism or tic disorders, in particular chronic schizophrenic psychoses and schizoaffective psychoses, temporary acute psychotic disorders, depressive episodes, recurring depressive episodes, manic episodes and bipolar affective disorders, which comprises administering a COX-2 (cyclooxygenase-2) inhibitor to a subject.

Moreover, the invention provides a method and composition for treating psychiatric disorders such as schizophrenia, delusional disorders, affective disorders, autism or tic disorders which comprises administering a COX-2 inhibitor in combination with a neuroleptic drug or an antidepressant to a subject.

(2) Description of Related Art

A relation between immunological dysfunctions and psychotic diseases, such as schizophrenia or affective disorders, has been discussed controversially over the last century.

In the case of schizophrenia for instance the pathogenesis is still unknown, but many findings indicate that schizophrenia is a syndrome based on different pathogenetic processes.

An inflammatory/immunological pathogenesis has-been discussed for a subgroup of schizophrenic patients (Yolken R H, Torrey E F: Viruses, schizophrenia, and bipolar disorder. Clin Microbiol Rev 1995; 8:131-145; Körschenhausen D, Hampel H, Ackenheil M, Penning R, Müller N: Fibrin degradation products in post mortem brain tissue of schizophrenics: a possible marker for underlying inflammatory processes, Schizophr Res 1996; 19: 103-109; Müller N, Ackenheil M: Psychoneuroimmunology and the cytokine-network in the CNS: implications for psychiatric disorders. Prog Neuropsychopharmacol & Biol Psychiat 1998; 22: 1-33). Studies showed that activating cytokines like interleukin-1 (IL-1) and IL-2 are increased in the cerebrospinal fluid of schizophrenic patients compared to controls (Sirota P, Schild K, ElizurA, Djaldetti M, Fishman P: Increased Interleukin-1 and Interleukin-3 like activity in schizophrenic patients. Prog Neuropsychopharmacol & Biol Psychiatry 1995; 19: 85-83; Licinio J, Seibyl, J P, Altemus M, Charney D S, Krystal J H: Elevated levels of Interleukin-2 in neuroleptic-free schizophrenics. Am J Psychiatry 1993; 150: 1408-1410), and that high levels of IL-2 in the cerebrospinal fluid are a predictor for the increased probability of a schizophrenic relapse (McAllister C G, van Kamen D P, Rehn T J, Miller A L, Gurklis J, Kelley M E, Yao J, Peters J L: Increases in CSF levels of Interleukin-2 in schizophrenia: effects of recurrence of psychosis and medication status. Am J Psychiatry 1995; 152: 1291-1297).

On the other hand, in a subgroup of schizophrenic patients a decreased immune response compared to controls has been observed, possibly due to a disturbance of antigen-presentation or antigen-recognition (Schwarz M J, Riedel M, Ackenheil M, MUller N: Decreased levels of soluble intercellular adhesion molecule -1 (slCAM-1) in unmedicated and medicated schizophrenic patients. Biol Psychiatry 2000; 47: 29-33), e.g. the increased immune reaction in the central nervous system may not be adequately regulated by an immune reaction in the peripheral immune system. This was observed mostly in acute schizophrenic patients presenting a recent onset of the disorder.

Another group of schizophrenic patients, however, seems to present an over-activation of the peripheral immune system in the sense of autoimmune processes (Radaport M H, Müller N: Immunological states associated with schizophrenia. In: Ader R, Felten D L, Cohen N (eds) Psychoneuroimmunology, Third Edition. Vol. 2, San Diego, Academic Press, 2001; pp 373-382; Radaport M H, McAllister C G, Kim Y S, Han J H, Pickar D, Nelson D M, Kirch D G, Paul S M: Increased soluble Interleukin-2 receptors in Caucasian and korean schizophrenic patients. Biol Psychiatry 1994; 35: 767-771). In several studies, increased titers of antibodies against the heat-shock-protein 60 were observed (Kilidireas K, Latov N, Strauss D H, Aviva D G, Hashim G A, Gorman J M, Sadiq S A: Antibodies to human 60 KD hear-shock protein in patients with schizophrenia. Lancet 1992; 340: 569-572), the increase being accompanied by increased soluble IL-2 receptors in the serum and increased titers of the soluble adhesion molecule SlCAM-1 (Radaport M H, Müller N: Immunological states associated with schizophrenia. In: Ader R, Felten D L, Cohen N (eds) Psychoneuroimmunology, Third Edition. Vol. 2, San Diego, Academic Press, 2001; pp 373-382; Schwarz M J, Riedel M, Gruber R, Ackenheil M, Müller N: Antibodies to heat-shock proteins in schizophrenic patients—Implications for disease mechanism. Am J Psychiatry 1999; 156, 1103, 1104). The close relationship between high sVCAM-1 titers and more pronounced schizophrenic negative symptoms (Schwarz M J, Riedel M, Gruber R, Ackenheil M, Müller N: Levels of soluble adhesion molecules in schizophrenia: Relation to psychopathology. In: N. Müller (Hrg) Psychiatry, Psychoneuroimmunology, and Viruses. Springer Verlag Wien, 1999; NY, pp. 121-130) as well as between high IgG levels in the cerebrospinal fluid and more pronounced negative symptoms further support this observation (Müller N, Ackenheil M: Immunoglobulin and albumin contents of cerebrospinal fluid in schizophrenic patients: The relationship to negative sympomatology. Schizophrenia Res 1995; 14: 223-228).

Affective diseases, in particular depressive diseases, may also have an inflammatory genesis. This is manifested in the fact that general inflammatory diseases are accompanied by depressive syndromes to an increased extent as well as in the fact that in depressive diseases, signs of inflammation occur more frequently in comparison to psychologically healthy persons. Scientifically, this was expressed in the monocyte/macrophage hypothesis of depression.

The occurrence of tics as well as of autism has also been discussed in many cases as a consequence of inflammatory processes.

The invention is based on the idea that substances with immunomodulatory properties could be used for the treatment of psychiatric disorders such as schizophrenia, delusional disorders, affective disorders, autism or tic disorders, which are at least partially based on immunological pathogenetic processes.

Recently, significant progress has been made in the field of inflammation and the development of drugs for the treatment of the inflammation-related disorders of osteoarthritis and rheumatoid arthritis. It has been known for some time that many of the common non-steroidal antiinflammatory drugs (NSAIDs) NSAIDs modulate prostaglandin synthesis by inhibition of cyclooxygenases that catalyze the transformation of arachidonic acid—the first step in the prostaglandin synthesis pathway. However, the use of high doses of many common NSAIDs can produce severe side effects that limit their therapeutic potential. In an effort to reduce the unwanted side effects of common NSAIDS, it was discovered that two cyclooxygenases are involved in the transformation of arachidonic acid as the first step in the prostaglandin synthesis pathway. These enzymes have been termed cyclooxygenase-1 (COX-1) and cyclooxygenase-2 (COX-2)(Needleman, P. et al., *J. Rheumatol.*, 24, *Suppl*.49:6-8 (1997);Fu, J.Y., et al., *J. Biol. Chem.*, 265(28):16737-40 (1990)). COX-1 has been shown to be a constitutively produced enzyme that is involved in many of the non-inflammatory regulatory functions associated with prostaglandins. COX-2, on the other hand, is an inducible enzyme having significant involvement in the inflammatory process. Inflammation causes the induction of COX-2, leading to the release of prostanoids, which sensitize peripheral nociceptor terminals and produce localized pain hypersensitivity (Samad, T. A. et al., *Nature,* 410 (6827):471-5 (2001)). Many of the common NSAIDs are now known to be inhibitors of both COX-1 and COX-2. Accordingly, when administered in sufficiently high levels, these NSAIDs affect not only the inflammatory consequences of COX-2 activity, but also the beneficial activities of COX-1. Recently, compounds that selectively inhibit COX-2 to a greater extent than the activity of COX-1 have been discovered. These new COX-2 inhibitors are believed to offer advantages that include the capacity to prevent or reduce inflammation while avoiding harmful side effects associated with the inhibition of COX-1, such as gastrointestinal and renal side effects, as well as inhibition of thrombocyte aggregation.

The use of COX-2 inhibitors in the therapy of arthritis and related indications is known. U.S. Pat. No. 5,760,068 describes the use of COX-2 inhibitors for the treatment of rheumatoid arthritis and osteoarthritis. WO 00/32189 discloses the preparation of pharmaceutical compositions containing the COX-2 inhibitor celecoxib and the use of celecoxib for the treatment of rheumatoid arthritis or as a painkiller.

Recently, progresses have also been made in the field of psychiatric disorders. For example, in the treatment of schizophrenia, a number of neuroleptic drugs (so-called classical and a typical neuroleptics) have become available, among which the more recent a typical neuroleptics excel by comparatively good effectiveness with a more favorable side effect profile. Unlike the classical neuroleptics, which are mainly effective for treating the positive symptoms of schizophrenia, the a typical neuroleptics improve both positive symptoms (hallucinations, delusions, and conceptual disorganization) and negative symptoms (apathy, social withdrawal, affective flattening, and poverty of speech) of schizophrenia. Plus, presumably due to their altered receptor binding profile, the a typicals cause minimal extrapyramidal symptoms and rarely cause tardive dyskinesias. Anyhow, neuroleptics in general act as syndrome oriented therapy and less as a causal therapy.

Therefore, a need exists for improved methods and compositions for the treatment of psychiatric disorders such as schizophrenia, delusional disorders, affective disorders, autism or tic disorders. In particular, it would be useful if such methods of treatment for disorders such as schizophrenia could be provided so that they reduced or avoided unwanted side effects.

SUMMARY OF THE INVENTION

Therefore, the present invention is directed to a novel method for the prevention, treatment, or inhibition of a psychiatric disorder such as schizophrenia, delusional disorders, affective disorders, autism or tic disorders in a subject in need of such prevention, treatment, or inhibition, the method comprising administering to the subject a COX-2 inhibitor or prodrug thereof.

Furthermore, the invention is concerned with a novel method for the prevention, treatment, or inhibition of a psychiatric disorder in a subject in need of such prevention, treatment, or inhibition, the method comprising administering to the subject a neuroleptic agent or antidepressant and a COX-2 inhibitor or prodrug thereof.

The invention is also directed to a novel composition for the treatment, prevention, or inhibition of a psychiatric disorder comprising a neuroleptic agent or antidepressant and a COX-2 inhibitor or prodrug thereof.

The invention is further directed to a novel kit that is suitable for use in the treatment of psychiatric disorders such as schizophrenia, delusional disorders, affective disorders, autism or tic disorders, the kit comprising a first dosage form comprising a neuroleptic or antidepressant and a second dosage form comprising a COX-2 inhibitor, in quantities which comprise a therapeutically effective amount of the combination of the compounds for the treatment, prevention, or inhibition of a psychiatric disorder, for simultaneous, separate or sequential administration.

Among the several advantages found to be achieved by the present invention, therefore, may be noted the provision of treatment methods for psychiatric disorders that comprise administering COX-2 inhibitors, the provision of such methods and compositions that combine the effectiveness of neuroleptic agents or antidepressants and COX-2 inhibitors, and the provision of such methods and compositions for the treatment of disorders such as schizophrenia that can reduce or avoid unwanted side effects.

DETAILED DESCRIPTION OF THE PREFERRED EMBODIMENTS

In accordance with the present invention, it has been discovered that psychiatric disorders can be prevented, treated or inhibited in-subjects in need of such prevention, treatment, or inhibition by administering to the subject a COX-2 inhibitor or prodrug thereof. Furthermore, it was discovered that psychiatric disorders can be prevented, treated or inhibited in subjects in need of such prevention, treatment, or inhibition by administering to the subject a neuroleptic agent or antidepressant in combination with a COX-2 inhibitor or prodrug thereof. It is believed that the novel combination of the neuroleptic agent or antidepressant and the COX-2 inhibitor are as efficacious as, and, in preferred embodiments, superior to, known and existing medications and treatment methods for psychiatric disorders, and that they offer such efficacy with reduced undesirable side effects. Kits that contain the novel combinations of a neuroleptic agent or antidepressant and the COX-2 inhibitor are also considered to be a part of the present invention.

The COX-2 inhibitors used in the present invention belong to the class of nonsteroidal anti-inflammatory drugs (NSAIDs). The term COX-2 inhibitor embraces compounds which selectively inhibit cyclooxygenase-2 over cyclooxygenase-1, and also includes pharmaceutically acceptable salts thereof. Also included within the scope of the present invention are compounds that act as prodrugs of cyclooxygenase-2-selective inhibitors. As used herein in reference to COX-2 inhibitors, the term "prodrug" refers to a chemical compound that can be converted into an active COX-2 inhibitor by metabolic or simple chemical processes within the body of the subject.

The COX-2 inhibitor of the present invention can be, for example, the COX-2 inhibitor meloxicam, Formula B-1 (CAS registry number 71125-38-7), or a pharmaceutically acceptable salt or prodrug thereof.

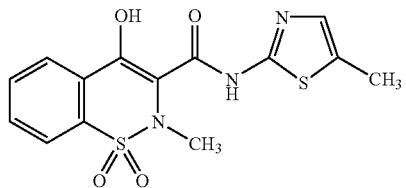

In another embodiment of the invention the COX-2 inhibitor can be the COX-2 inhibitor RS 57067, 6-[[5-(4-chlorobenzoyl)-1,4-dimethyl-1H-pyrrol-2-yl]methyl]-3(2H)-pyridazinone, Formula B-2 (CAS registry number 179382-91-3), or a pharmaceutically acceptable salt or prodrug thereof.

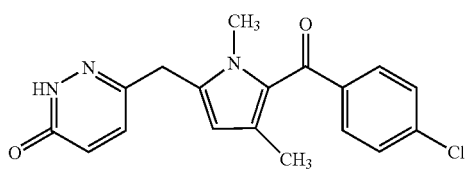

In a preferred embodiment of the invention the COX-2 inhibitor is a chromene derivative, that is a substituted benzopyran or a substituted benzopyran analog, and even more preferably selected from the group consisting of substituted benzothiopyrans, dihydroquinolines, or dihydronaphthalenes having the structure of any one of the compounds having a structure shown by general Formulas I, II, or III, shown below, and possessing, by way of example and not limitation, the structures disclosed in Table 1, including the diastereomers, enantiomers, racemates, tautomers, salts, esters, amides and prodrugs thereof.

Benzopyran COX-2 inhibitors useful in the practice of the present invention are described in U.S. Pat. No. 6,034,256 and 6,077,850.

Formula I is:

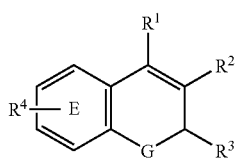

wherein G is selected from the group consisting of O or S or $NR^a$;
wherein $R^a$ is alkyl;
wherein $R^1$ is selected from the group consisting of H and aryl;
wherein $R^2$ is selected from the group consisting of carboxyl, aminocarbonyl, alkylsulfonylaminocarbonyl and alkoxycarbonyl;
wherein $R^3$ is selected from the group consisting of haloalkyl, alkyl, aralkyl, cycloalkyl and aryl optionally substituted with one or more radicals selected from alkylthio, nitro and alkylsulfonyl; and wherein $R^4$ is selected from the group consisting of one or more radicals selected from H, halo, alkyl, aralkyl, alkoxy, aryloxy, heteroaryloxy, aralkyloxy, heteroaralkyloxy, haloalkyl, haloalkoxy, alkylamino, arylamino, aralkylamino, heteroarylamino, heteroarylalkylamino, nitro, amino, aminosulfonyl, alkylaminosulfonyl, arylaminosulfonyl, heteroarylaminosulfonyl, aralkylaminosulfonyl, heteroaralkylaminosulfonyl, heterocyclosulfonyl, alkylsulfonyl, hydroxyarylcarbonyl, nitroaryl, optionally substituted aryl, optionally substituted heteroaryl, aralkylcarbonyl, heteroarylcarbonyl, arylcarbonyl, aminocarbonyl, and alkylcarbonyl;
or wherein $R^4$ together with ring E forms a naphthyl radical; or an isomer or pharmaceutically acceptable salt thereof; and
including the diastereomers, enantiomers, racemates, tautomers, salts, esters, amides and prodrugs thereof.

Formula II is:

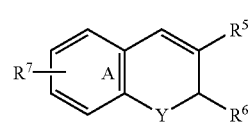

wherein:
Y is selected from the group consisting of O or S or $NR^b$;
$R^b$ is alkyl;
$R^5$ is selected from the group consisting of carboxyl, aminocarbonyl, alkylsulfonylaminocarbonyl and alkoxycarbonyl;
$R^6$ is selected from the group consisting of haloalkyl, alkyl, aralkyl, cycloalkyl and aryl, wherein haloalkyl, alkyl, aralkyl, cycloalkyl, and aryl each is independently optionally substituted with one or more radicals selected from the group consisting of alkylthio, nitro and alkylsulfonyl; and
$R^7$ is one or more radicals selected from the group consisting of hydrido, halo, alkyl, aralkyl, alkoxy, aryloxy, heteroaryloxy, aralkyloxy, heteroaralkyloxy, haloalkyl, haloalkoxy, alkylamino, arylamino, aralkylamino, heteroarylamino, heteroarylalkylamino, nitro, amino, aminosulfonyl, alkylaminosulfonyl, arylaminosulfonyl, heteroarylaminosulfonyl, aralkylaminosulfonyl, heteroaralkylaminosulfonyl, heterocyclosulfonyl, alkylsulfonyl, optionally substituted aryl, optionally substituted heteroaryl, aralkylcarbonyl, heteroarylcarbonyl, arylcarbonyl, aminocarbonyl, and alkylcarbonyl; or wherein $R^7$ together with ring A forms a naphthyl radical;
or an isomer or pharmaceutically acceptable salt thereof.

The COX-2 inhibitor may also be a compound of Formula II, wherein:
Y is selected from the group consisting of oxygen and sulfur;
$R^5$ is selected from the group consisting of carboxyl, lower alkyl, lower aralkyl and lower alkoxycarbonyl;
$R^6$ is selected from the group consisting of lower haloalkyl, lower cycloalkyl and phenyl; and
$R^7$ is one or more radicals selected from the group of consisting of hydrido, halo, lower alkyl, lower alkoxy, lower haloalkyl, lower haloalkoxy, lower alkylamino, nitro, amino, aminosulfonyl, lower alkylaminosulfonyl, 5-membered heteroarylalkylaminosulfonyl, 6-membered heteroarylalkylaminosulfonyl, lower aralkylaminosulfonyl, 5-membered nitrogen-containing heterocyclosulfonyl, 6-membered-nitrogen containing heterocyclosulfonyl, lower alkylsulfonyl, optionally substituted phenyl, lower aralkylcarbonyl, and lower alkylcarbonyl; or wherein $R^7$ together with ring A forms a naphthyl radical; or an isomer or pharmaceutically acceptable salt thereof.

The COX-2 inhibitor may also be a compound of Formula II, wherein:

$R^5$ is carboxyl;

$R^6$ is lower haloalkyl; and $R^7$ is one or more radicals selected from the group consisting of hydrido, halo, lower alkyl, lower haloalkyl, lower haloalkoxy, lower alkylamino, amino, aminosulfonyl, lower alkylaminosulfonyl, 5-membered heteroarylalkylaminosulfonyl, 6-membered heteroarylalkylaminosulfonyl, lower aralkylaminosulfonyl, lower alkylsulfonyl, 6-membered nitrogen-containing heterocyclosulfonyl, optionally substituted phenyl, lower aralkylcarbonyl, and lower alkylcarbonyl; or wherein $R^7$ together with ring A forms a naphthyl radical;

or an isomer or pharmaceutically acceptable salt thereof.

The COX-2 inhibitor may also be a compound of Formula II, wherein:

$R^6$ is selected from the group consisting of fluoromethyl, chloromethyl, dichloromethyl, trichloromethyl, pentafluoroethyl, heptafluoropropyl, difluoroethyl, difluoropropyl, dichloroethyl, dichloropropyl, difluoromethyl, and trifluoromethyl; and $R^7$ is one or more radicals selected from the group consisting of hydrido, chloro, fluoro, bromo, iodo, methyl, ethyl, isopropyl, tert-butyl, butyl, isobutyl, pentyl, hexyl, methoxy, ethoxy, isopropyloxy, tertbutyloxy, trifluoromethyl, difluoromethyl, trifluoromethoxy, amino, N,N-dimethylamino, N,N-diethylamino, N-phenylmethylaminosulfonyl, N-phenylethylaminosulfonyl, N-(2-furylmethyl)aminosulfonyl, nitro, N,N-dimethylaminosulfonyl, aminosulfonyl, N-methylaminosulfonyl, N-ethylsulfonyl, 2,2-dimethylethylaminosulfonyl, N,N-dimethylaminosulfonyl, N-(2-methylpropyl)aminosulfonyl, N-morpholinosulfonyl, methylsulfonyl, benzylcarbonyl, 2,2-dimethylpropylcarbonyl, phenylacetyl and phenyl;

or wherein $R^2$ together with ring A forms a naphthyl radical;

or an isomer or pharmaceutically acceptable salt thereof.

The COX-2 inhibitor may also be a compound of Formula II, wherein:

$R^6$ is selected from the group consisting trifluoromethyl and pentafluoroethyl; and $R^7$ is one or more radicals selected from the group consisting of hydrido, chloro, fluoro, bromo, iodo, methyl, ethyl, isopropyl, tert-butyl, methoxy, trifluoromethyl, trifluoromethoxy, N-phenylmethylaminosulfonyl, N-phenylethylaminosulfonyl, N-(2-furylmethyl)aminosulfonyl, N,N-dimethylaminosulfonyl, N-methylaminosulfonyl, N-(2,2-dimethylethyl)aminosulfonyl, dimethylaminosulfonyl, 2-methylpropylaminosulfonyl, N-morpholinosulfonyl, methylsulfonyl, benzylcarbonyl, and phenyl; or wherein $R^7$ together with ring A forms a naphthyl radical;

or an isomer or prodrug thereof.

The COX-2 inhibitor of the present invention can also be a compound having the structure of Formula III:

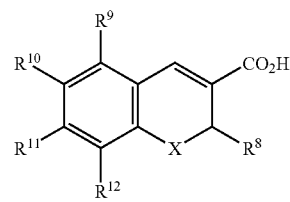

wherein:

X is selected from the group consisting of O and S;

$R^8$ is lower haloalkyl;

$R^9$ is selected from the group consisting of hydrido, and halo;

$R^{10}$ is selected from the group consisting of hydrido, halo, lower alkyl, lower haloalkoxy, lower alkoxy, lower aralkylcarbonyl, lower dialkylaminosulfonyl, lower alkylaminosulfonyl, lower aralkylaminosulfonyl, lower heteroaralkylaminosulfonyl, 5-membered nitrogen-containing heterocyclosulfonyl, and 6-membered nitrogen-containing heterocyclosulfonyl;

$R^{11}$ is selected from the group consisting of hydrido, lower alkyl, halo, lower alkoxy, and aryl; and $R^{12}$ is selected from the group consisting of the group consisting of hydrido, halo, lower alkyl, lower alkoxy, and aryl;

or an isomer or prodrug thereof.

The COX-2 inhibitor can also be a compound of having the structure of Formula III, wherein $R^8$ is selected from the group consisting of trifluoromethyl and pentafluoroethyl;

$R^9$ is selected from the group consisting of hydrido, chloro, and fluoro;

$R^{10}$ is selected from the group consisting of hydrido, chloro, bromo, fluoro, iodo, methyl, tert-butyl, trifluoromethoxy, methoxy, benzylcarbonyl, dimethylaminosulfonyl, isopropylaminosulfonyl, methylaminosulfonyl, benzylaminosulfonyl, phenylethylaminosulfonyl, methylpropylaminosulfonyl, methylsulfonyl, and morpholinosulfonyl;

$R^{11}$ is selected from the group consisting of hydrido, methyl, ethyl, isopropyl, tert-butyl, chloro, methoxy, diethylamino, and phenyl; and $R^{12}$ is selected from the group consisting of hydrido, chloro, bromo, fluoro, methyl, ethyl, tert-butyl, methoxy, and phenyl;

or an isomer or prodrug thereof.

TABLE 1

Examples of Chromene COX-2 Inhibitors as Embodiments

| Compound Number | Structural Formula |
|---|---|
| B-3 | ![structure] 6-Nitro-2-trifluoromethyl-2H-1-benzopyran-3-carboxylic acid |

TABLE 1-continued

Examples of Chromene COX-2 Inhibitors as Embodiments

| Compound Number | Structural Formula |
|---|---|
| B-4 | 6-Chloro-8-methyl-2-trifluoromethyl-2H-1-benzopyran-3-carboxylic acid |
| B-5 | ((S)-6-Chloro-7-(1,1-dimethylethyl)-2-(trifluoromethyl-2H-1-benzopyran-3-carboxylic acid |
| B-6 | 2-Trifluoromethyl-2H-naphtho[2,3-b]pyran-3-carboxylic acid |
| B-7 | 6-Chloro-7-(4-nitrophenoxy)-2-(trifluoromethyl)-2H-1-benzopyran-3-carboxylic acid |
| B-8 | ((S)-6,8-Dichloro-2-(trifluoromethyl)-2H-1-benzopyran-3-carboxylic acid |
| B-9 | 6-Chloro-2-(trifluoromethyl)-4-phenyl-2H-1-benzopyran-3-carboxylic acid |
| B-10 | 6-(4-Hydroxybenzoyl)-2-(trifluoromethyl)-2H-1-benzopyran-3-carboxylic acid |
| B-11 | 2-(Trifluoromethyl)-6-[(trifluoromethyl)thio]-2H-1-benzothiopyran-3-carboxylic acid |
| B-12 | 6,8-Dichloro-2-trifluoromethyl-2H-1-benzothiopyran-3-carboxylic acid |
| B-13 | 6-(1,1-Dimethylethyl)-2-(trifluoromethyl)-2H-1-benzothiopyran-3-carboxylic acid |
| B-14 | 6,7-Difluoro-1,2-dihydro-2-(trifluoromethyl)-3-quinolinecarboxylic acid |
| B-15 | 6-Chloro-1,2-dihydro-1-methyl-2-(trifluoromethyl)-3-quinolinecarboxylic acid |

TABLE 1-continued

Examples of Chromene COX-2 Inhibitors as Embodiments

Compound Number | Structural Formula

B-16

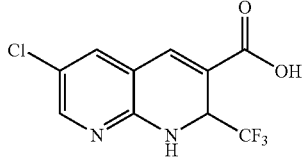

6-Chloro-2-(trifluoromethyl)-1,2-dihydro
[1,8]naphthyridine-3-carboxylic acid

B-17

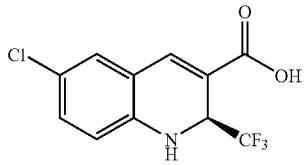

((S)-6-Chloro-1,2-dihydro-2-(trifluoro
methyl)-3-quinolinecarboxylic acid

Specific compounds that are useful for the COX-2 inhibitor include:

a1) 8-acetyl-3-(4-fluorophenyl)-2-(4-methylsulfonyl)phenyl-imidazo(1,2-a)pyridine;
a2) 5,5-dimethyl-4-(4-methylsulfonyl)phenyl-3-phenyl-2-(5H)-furanone;
a3) 5-(4-fluorophenyl)-1-[4-(methylsulfonyl)phenyl]-3-(trifluoromethyl)pyrazole;
a4) 4-(4-fluorophenyl)-5-[4-(methylsulfonyl)phenyl]-1-phenyl-3-(trifluoromethyl)pyrazole;
a5) 4-(5-(4-chlorophenyl)-3-(4-methoxyphenyl)-1H-pyrazol-1-yl)benzenesulfonamide;
a6) 4-(3,5-bis(4-methylphenyl)-1H-pyrazol-1-yl)benzenesulfonamide;
a7) 4-(5-(4-chlorophenyl)-3-phenyl-1H-pyrazol-1-yl)benzenesulfonamide;
a8) 4-(3,5-bis(4-methoxyphenyl)-1H-pyrazol-1-yl)benzenesulfonamide;
a9) 4-(5-(4-chlorophenyl)-3-(4-methylphenyl)-1H-pyrazol-1-yl)benzenesulfonamide;
a10) 4-(5-(4-chlorophenyl)-3-(4-nitrophenyl)-1H-pyrazol-1-yl)benzenesulfonamide;
b1) 4-(5-(4-chlorophenyl)-3-(5-chloro-2-thienyl)-1H-pyrazol-1-yl)benzenesulfonamide;
b2) 4-(4-chloro-3,5-diphenyl-1H-pyrazol-1-yl)benzenesulfonamide
b3) 4-[5-(4-chlorophenyl)-3-(trifluoromethyl)-1H-pyrazol-1-yl]benzenesulfonamide;
b4) 4-[5-phenyl-3-(trifluoromethyl)-1H-pyrazol-1-yl]benzenesulfonamide;
b5) 4-[5-(4-fluorophenyl)-3-(trifluoromethyl)-1H-pyrazol-1-yl]benzenesulfonamide;
b6) 4-[5-(4-methoxyphenyl)-3-(trifluoromethyl)-1H-pyrazol-1-yl]benzenesulfonamide;
b7) 4-[5-(4-chlorophenyl)-3-(difluoromethyl)-1H-pyrazol-1-yl]benzenesulfonamide;
b8) 4-[5-(4-methylphenyl)-3-(trifluoromethyl)-1H-pyrazol-1-yl]benzenesulfonamide;
b9) 4-[4-chloro-5-(4-chlorophenyl)-3-(trifluoromethyl)-1H-pyrazol-1-yl]benzenesulfonamide;
b10) 4-[3-(difluoromethyl)-5-(4-methylphenyl)-1H-pyrazol-1-yl]benzenesulfonamide;
c1) 4-[3-(difluoromethyl)-5-phenyl-1H-pyrazol-1-yl]benzenesulfonamide;
c2) 4-[3-(difluoromethyl)-5-(4-methoxyphenyl)-1H-pyrazol-1-yl]benzenesulfonamide;
c3) 4-[3-cyano-5-(4-fluorophenyl)-1H-pyrazol-1-yl]benzenesulfonamide;
c4) 4-[3-(difluoromethyl)-5-(3-fluoro-4-methoxyphenyl)-1H-pyrazol-1-yl]benzenesulfonamide;
c5) 4-[5-(3-fluoro-4-methoxyphenyl)-3-(trifluoromethyl)-1H-pyrazol-1-yl]benzenesulfonamide;
c6) 4-[4-chloro-5-phenyl-1H-pyrazol-1-yl]benzenesulfonamide;
c7) 4-[5-(4-chlorophenyl)-3-(hydroxymethyl)-1H-pyrazol-1-yl]benzenesulfonamide;
c8) 4-[5-(4-(N,N-dimethylamino)phenyl)-3-(trifluoromethyl)-1H-pyrazol-1-yl]benzenesulfonamide;
c9) 5-(4-fluorophenyl)-6-[4-(methylsulfonyl)phenyl]spiro[2.4]hept-5-ene;
c10) 4-[6-(4-fluorophenyl)spiro[2.4]hept-5-en-5-yl]benzenesulfonamide;
d1) 6-(4-fluorophenyl)-7-[4-(methylsulfonyl)phenyl]spiro[3.4]oct-6-ene;
d2) 5-(3-chloro-4-methoxyphenyl)-6-[4-(methylsulfonyl)phenyl]spiro[2.4]hept-5-ene;
d3) 4-[6-(3-chloro-4-methoxyphenyl)spiro[2.4]hept-5-en-5-yl]benzenesulfonamide;
d4) 5-(3,5-dichloro-4-methoxyphenyl)-6-[4-(methylsulfonyl)phenyl]spiro[2.4]hept-5-ene;
d5) 5-(3-chloro-4-fluorophenyl)-6-[4-(methylsulfonyl)phenyl]spiro[2.4]hept-5-ene;
d6) 4-[6-(3,4-dichlorophenyl)spiro[2.4]hept-5-en-5-yl]benzenesulfonamide;
d7) 2-(3-chloro-4-fluorophenyl)-4-(4-fluorophenyl)-5-(4-methylsulfonylphenyl)thiazole;
d8) 2-(2-chlorophenyl)-4-(4-fluorophenyl)-5-(4-methylsulfonylphenyl)thiazole;
d9) 5-(4-fluorophenyl)-4-(4-methylsulfonylphenyl)-2-methylthiazole;
d10) 4-(4-fluorophenyl)-5-(4-methylsulfonylphenyl)-2-trifluoromethylthiazole;
e1) 4-(4-fluorophenyl)-5-(4-methylsulfonylphenyl)-2-(2-thienyl)thiazole;
e2) 4-(4-fluorophenyl)-5-(4-methylsulfonylphenyl)-2-benzylaminothiazole;
e3) 4-(4-fluorophenyl)-5-(4-methylsulfonylphenyl)-2-(1-propylamino)thiazole;
e4) 2-[(3,5-dichlorophenoxy)methyl]-4-(4-fluorophenyl)-5-[4-(methylsulfonyl)phenyl]thiazole;
e5) 5-(4-fluorophenyl)-4-(4-methylsulfonylphenyl)-2-trifluoromethylthiazole;
e6) 1-methylsulfonyl-[1,1-dimethyl-4-(4-fluorophenyl)cyclopenta-2,4-dien-3-yl]benzene;
e7) 4-[4-(4-fluorophenyl)-1,1-dimethylcyclopenta-2,4-dien-3-yl]benzenesulfonamide;
e8) 5-(4-fluorophenyl)-6-[4-(methylsulfonyl)phenyl]spiro[2.4]hepta-4,6-diene;
e9) 4-[6-(4-fluorophenyl)spiro[2.4]hepta4,6-dien-5-yl]benzenesulfonamide;
e10) 6-(4-fluorophenyl)-2-methoxy-5-[4-(methylsulfonyl)phenyl]-pyridine-3-carbonitrile;
f1) 2-bromo-6-(4-fluorophenyl)-5-[4-(methylsulfonyl)phenyl]-pyridine-3-carbonitrile;
f2) 6-(4-fluorophenyl)-5-[4-(methylsulfonyl)phenyl]-2-phenyl-pyridine-3-carbonitrile;

f3) 4-[2-(4-methylpyridin-2-yl)-4-(trifluoromethyl)-1H-imidazol-1-yl]benzenesulfonamide;
f4) 4-[2-(5-methylpyridin-3-yl)4-(trifluoromethyl)-1H-imidazol-1-yl]benzenesulfonamide;
f5) 4-[2-(2-methylpyridin-3-yl)$_4$-(trifluoromethyl)-1H-imidazol-1-yl]benzenesulfonamide;
f6) 3-[1-[4-(methylsulfonyl)phenyl]-4-(trifluoromethyl)-1H-imidazol-2-yl]pyridine;
f7) 2-[1-[4-(methylsulfonyl)phenyl-4-(trifluoromethyl)-1H-imidazol-2-yl]pyridine;
f8) 2-methyl-4-[1-[4-(methylsulfonyl)phenyl-4-(trifluoromethyl)-1H-imidazol-2-yl]pyridine;
f9) 2-methyl-6-[1-[4-(methylsulfonyl)phenyl-4-(trifluoromethyl)-1H-imidazol-2-yl]pyridine;
f10) 4-[2-(6-methylpyridin-3-yl)-4-(trifluoromethyl)-1H-imidazol-1-yl]benzenesulfonamide;
g1) 2-(3,4-difluorophenyl)-1-[4-(methylsulfonyl)phenyl]-4-(trifluoromethyl)-1H-imidazole;
g2) 4-[2-(4-methylphenyl)$_4$-(trifluoromethyl)-1H-imidazol-1-yl]benzenesulfonamide;
g3) 2-(4-chlorophenyl)-1-[4-(methylsulfonyl)phenyl]-4-methyl-1H-imidazole;
g4) 2-(4-chlorophenyl)-1-[4-(methylsulfonyl)phenyl]-4-phenyl-1H-imidazole;
g5) 2-(4-chlorophenyl)-4-(4-fluorophenyl)-1-(4-(methylsulfonyl)phenyl]-1H-imidazole;
g6) 2-(3-fluoro-4-methoxyphenyl)-1-[4-(methylsulfonyl)phenyl4-(trifluoromethyl)-1H-imidazole;
g7) 1-[4-(methylsulfonyl)phenyl]-2-phenyl-4-trifluoromethyl-1H-imidazole;
g8) 2-(4-methylphenyl)-1-[4-(methylsulfonyl)phenyl]4-trifluoromethyl-1H-imidazole;
g9) 4-[2-(3-chloro-4-methylphenyl)-4-(trifluoromethyl)-1H-imidazol-1-yl]benzenesulfonamide;
g 10) 2-(3-fluoro-5-methylphenyl)-1-[4-(methylsulfonyl)phenyl]-4-(trifluoromethyl)-1H-imidazole;
h1) 4-[2-(3-fluoro-5-methylphenyl)4-(trifluoromethyl)-1H-imidazol-1-yl]benzenesulfonamide;
h2) 2-(3-methylphenyl)-1-[4-(methylsulfonyl)phenyl]-4-trifluoromethyl-1H-imidazole;
h3) 4-[2-(3-methylphenyl)$_4$-trifluoromethyl-1H-imidazol-1-yl]benzenesulfonamide;
h4) 1-[4-(methylsulfonyl)phenyl]-2-(3-chlorophenyl)-4-trifluoromethyl-1H-imidazole;
h5) 4-[2-(3-chlorophenyl)-4-trifluoromethyl-1H-imidazol-1-yl]benzenesulfonamide;
h6) 4-[2-phenyl-4-trifluoromethyl-1H-imidazol-1-yl]benzenesulfonamide;
h7) 4-[2-(4-methoxy-3-chlorophenyl)-4-trifluoromethyl-1H-imidazol-1-yl]benzenesulfonamide;
h8) 1-ally-4-(4-fluorophenyl)-3-[4-(methylsulfonyl)phenyl]-5-(trifluoromethyl)-1H-pyrazole;
h10) 4-[1-ethyl-4-(4-fluorophenyl)-5-(trifluoromethyl)-1H-pyrazol-3-yl]benzenesulfonamide;
i1) N-phenyl-[4-(4-luorophenyl)-3-[4-(methylsulfonyl)phenyl]-5-(trifluoromethyl)-1H-pyrazol-1-yl]acetamide;
i2) ethyl [4-(4-fluorophenyl)-3-[4-(methylsulfonyl)phenyl]-5-(trifluoromethyl)-1H-pyrazol-1-yl]acetate;
i3) 4-(4-fluorophenyl)-3-[4-(methylsulfonyl)phenyl]-1-(2-phenylethyl)-1H-pyrazole;
i4) 4-(4-fluorophenyl)-3-[4-(methylsulfonyl)phenyl]-1-(2-phenylethyl)-5-(trifluoromethyl)pyrazole;
i5) 1-ethyl-4-(4-fluorophenyl)-3-[4-(methylsulfonyl)phenyl]-5-(trifluoromethyl)-1H-pyrazole;
i6) 5-(4-fluorophenyl)-4-(4-methylsulfonylphenyl)-2-trifluoromethyl-1H-imidazole;
i7) 4-[4-(methylsulfonyl)phenyl]-5-(2-thiophenyl)-2-(trifluoromethyl)-1H-imidazole;
i8) 5-(4-fluorophenyl)-2-methoxy-4-[4-(methylsulfonyl)phenyl]-6-(trifluoromethyl)pyridine;
i9) 2-ethoxy-5-(4-fluorophenyl)-4-[4-(methylsulfonyl)phenyl]-6-(trifluoromethyl)pyridine;
i10) 5-(4-fluorophenyl)-4-[4-(methylsulfonyl)phenyl]-2-(2-propynyloxy)-6-(trifluoromethyl)pyridine;
j1) 2-bromo-5-(4-fluorophenyl)-4-[4-(methylsulfonyl)phenyl]-6-(trifluoromethyl)pyridine;
j2) 4-[2-(3-chloro-4-methoxyphenyl)-4,5-difluorophenyl]benzenesulfonamide;
j3) 1-(4-fluorophenyl)-2-[4-(methylsulfonyl)phenyl]benzene;
j4) 5-difluoromethyl4-(4-methylsulfonylphenyl)-3-phenyl-isoxazole;
j5) 4-[3-ethyl-5-phenylisoxazol-4-yl]benzenesulfonamide;
j6) 4-[5-difluoromethyl-3-phenylisoxazol-4-yl]benzenesulfonamide;
j7) 4-[5-hydroxymethyl-3-phenylisoxazol-4-yl]benzenesulfonamide;
j8) 4-[5-methyl-3-phenyl-isoxazol-4-yl]benzenesulfonamide;
j9) 1-[2-(4-fluorophenyl)cyclopenten-1-yl]-4-(methylsulfonyl)benzene;
j10) 1-[2-(4-fluoro-2-methylphenyl)cyclopenten-1-yl]-4-(methylsulfonyl)benzene;
k1) 1-[2-(4-chlorophenyl)cyclopenten-1-yl]4-(methylsulfonyl)benzene;
k2) 1-[2-(2,4-dichlorophenyl)cyclopenten-1-yl]4-(methylsulfonyl)benzene;
k3) 1-[2-(4-trifluoromethylphenyl)cyclopenten-1-yl]4-(methylsulfonyl)benzene;
k4) 1-[2-(4-methylthiophenyl)cyclopenten-1-yl]-4-(methylsulfonyl)benzene;
k5) 1-[2-(4-fluorophenyl)4,4-dimethylcyclopenten-1-yl]4-(methylsulfonyl)benzene;
k6) 4-[2-(4-fluorophenyl)4,4-dimethylcyclopenten-1-yl]benzenesulfonamide;
k7) i-[2-(4-chlorophenyl)-4,4-dimethylcyclopenten-1-yl]4-(methylsulfonyl)benzene;
k8) 4-[2-(4-chlorophenyl)4,4-dimethylcyclopenten-1-yl]benzenesulfonamide;
k9) 4-[2-(4-fluorophenyl)cyclopenten-1-yl]benzenesulfonamide;
k10) 4-[2-(4-chlorophenyl)cyclopenten-1-yl]benzenesulfonamide;
l1) 1-[2-(4-methoxyphenyl)cyclopenten-1-yl]4-(methylsulfonyl)benzene;
l2) 1-[2-(2,3-difluorophenyl)cyclopenten-1-yl]4-(methylsulfonyl)benzene;
l3) 4-[2-(3-fluoro-4-methoxyphenyl)cyclopenten-1-yl]benzenesulfonamide;
l4) 1-[2-(3-chloro4-methoxyphenyl)cyclopenten-1-yl]-4-(methylsulfonyl)benzene;
l5) 4-[2-(3-chloro-4-fluorophenyl)cyclopenten-1-yl]benzenesulfonamide;
l6) 4-[2-(2-methylpyridin-5-yl)cyclopenten-1-yl]benzenesulfonamide;
l7) ethyl 2-[4-(4-fluorophenyl)-5-[4-(methylsulfonyl)phenyl]oxazol-2-yl]-2-benzyl-acetate;
l8) 2-[4-(4-fluorophenyl)-5-[4-(methylsulfonyl)phenyl]oxazol-2-yl]acetic acid;
l9) 2-(tert-butyl)-4-(4-fluorophenyl)-5-[4-(methylsulfonyl)phenyl]oxazole;
l10) 4-(4-fluorophenyl)-5-[4-(methylsulfonyl)phenyl]-2-phenyloxazole;

m1) 4-(4-fluorophenyl)-2-methyl-5-[4-(methylsulfonyl)phenyl]oxazole; and
m2) 4-[5-(3-fluoro-4-methoxyphenyl)-2-trifluoromethyl4-oxazolyl]benzenesulfonamide.
m3) 6-chloro-2-trifluoromethyl-2H-1-benzopyran-3-carboxylic acid;
m4) 6-chloro-7-methyl-2-trifluoromethyl-2H-1-benzopyran-3-carboxylic acid;
m5) 8-(1-methylethyl)-2-trifluoromethyl-2H-1-benzopyran-3-carboxylic acid;
m6) 6-chloro-7-(1,1-dimethylethyl)-2-trifluoromethyl-2H-1-benzopyran-3-carboxylic acid;
m7) 6-chloro-8-(1-methylethyl)-2-trifluoromethyl-2H-1-benzopyran-3-carboxylic acid;
m8) 2-trifluoromethyl-3H-naphthopyran-3-carboxylic acid;
m9) 7-(1,1-dimethylethyl)-2-trifluoromethyl-2H-1-benzopyran-3-carboxylic acid;
m10) 6-bromo-2-trifluoromethyl-2H-1-benzopyran-3-carboxylic acid;
n1) 8-chloro-2-trifluoromethyl-2H-1-benzopyran-3-carboxylic acid;
n2) 6-trifluoromethoxy-2-trifluoromethyl-2H-1-benzopyran-3-carboxylic acid;
n3) 5,7-dichloro-2-trifluoromethyl-2H-1-benzopyran-3-carboxylic acid;
n4) 8-phenyl-2-trifluoromethyl-2H-1-benzopyran-3-carboxylic acid;
n5) 7,8-dimethyl-2-trifluoromethyl-2H-1-benzopyran-3-carboxylic acid;
n6) 6,8-bis(dimethylethyl)-2-trifluoromethyl-2H-1-benzopyran-3-carboxylic acid;
n7) 7-(1-methylethyl)-2-trifluoromethyl-2H-1-benzopyran-3-carboxylic acid;
n8) 7-phenyl-2-trifluoromethyl-2H-1-benzopyran-3-carboxylic acid;
n9) 6-chloro-7-ethyl-2-trifluoromethyl-2H-1-benzopyran-3-carboxylic acid;
n10) 6-chloro-8-ethyl-2-trifluoromethyl-2H-1-benzopyran-3-carboxylic acid;
o1) 6-chloro-7-phenyl-2-trifluoromethyl-2H-1-benzopyran-3-carboxylic acid;
o2) 6,7-dichloro-2-trifluoromethyl-2H-1-benzopyran-3-carboxylic acid;
o3) 6,8-dichloro-2-trifluoromethyl-2H-1-benzopyran-3-carboxylic acid;
o4) 2-trifluoromethyl-3H-naptho[2,1-b]pyran-3-carboxylic acid;
o5) 6-chloro-8-methyl-2-trifluoromethyl-2H-1-benzopyran-3-carboxylic acid;
o6) 8-chloro-6-methyl-2-trifluoromethyl-2H-1-benzopyran-3-carboxylic acid;
o7) 8-chloro-6-methoxy-2-trifluoromethyl-2H-1-benzopyran-3-carboxylic acid;
o8) 6-bromo-8-choro-2-trifluoromethyl-2H-1-benzopyran-3-carboxylic acid;
o9) 8-bromo-6-fluoro-2-trifluoromethyl-2H-1-benzopyran-3-carboxylic acid;
o10) 8-bromo-6-methyl-2-trifluoromethyl-2H-1-benzopyran-3-carboxylic acid;
p1) 8-bromo-5-fluoro-2-trifluoromethyl-2H-1-benzopyran-3-carboxylic acid;
p2) 6-chloro-8-fluoro-2-trifluoromethyl-2H-1-benzopyran-3-carboxylic acid;
p3) 6-bromo-8-methoxy-2-trifluoromethyl-2H-1-benzopyran-3-carboxylic acid;
p4) 6-[[(phenylmethyl)amino]sulfonyl]-2-trifluoromethyl-2H-1-benzopyran-3-carboxylic acid;
p5) 6-[(dimethylamino)sulfonyl]-2-trifluoromethyl-2H-1-benzopyran-3-carboxylic acid;
p6) 6-[(methylamino)sulfonyl]-2-trifluoromethyl-2H-1-benzopyran-3-carboxylic acid;
p7) 6-[(4-morpholino)sulfonyl]-2-trifluoromethyl-2H-1-benzopyran-3-carboxylic acid;
p8) 6-[(1,1-dimethylethyl)aminosulfonyl]-2-trifluoromethyl-2H-1-benzopyran-3-carboxylic acid;
p9) 6-[(2-methylpropyl)aminosulfonyl]-2-trifluoromethyl-2H-1-benzopyran-3-carboxylic acid;
p10) 6-methylsulfonyl-2-trifluoromethyl-2H-1-benzopyran-3-carboxylic acid;
q1) 8-chloro-6-[[(phenylmethyl)amino]sulfonyl]-2-trifluoromethyl-2H-1-benzopyran-3-carboxylic acid;
q2) 6-phenylacetyl-2-trifluoromethyl-2H-1-benzopyran-3-carboxylic acid;
q3) 6,8-dibromo-2-trifluoromethyl-2H-1-benzopyran-3-carboxylic acid;
q4) 8-chloro-5,6-dimethyl-2-tri fluoromethyl-2H-1-benzopyran-3-carboxylic acid;
q4) 6,8-dichloro-(S)-2-trifluoromethyl-2H-1-benzopyran-3-carboxylic acid;
q6) 6-benzylsulfonyl-2-trifluoromethyl-2H-1-benzopyran-3-carboxylic acid;
q7) 6-[[N-(2-furylmethyl)amino]sulfonyl]-2-trifluoromethyl-2H-1-benzopyran-3-carboxylic acid;
q8) 6-[[N-(2-phenylethyl)amino]sulfonyl]-2-trifluoromethyl-2H-1-benzopyran-3-carboxylic acid;
q9) 6-iodo-2-trifluoromethyl-2H-1-benzopyran-3-carboxylic acid;
q10) 7-(1,1-dimethylethyl)-2-pentafluoroethyl-2H-1-benzopyran-3-carboxylic acid;
r1) 5,5-dimethyl-3-(3-fluorophenyl)-4-(4-methyl-sulphonyl-2(5H)-fluranone;
r2) 6-chloro-2-trifluoromethyl-2H-1-benzothiopyran-3-carboxylic acid;
r3) 4-[5-(4-chlorophenyl)-3-(trifluoromethyl)-1H-pyrazol-1-yl]benzenesulfonamide;
r4) 4-[5-(4-methylphenyl)-3-(trifluoromethyl)-1H-pyrazol-1-yl]benzenesulfonamide;
r5) 4-[5-(3-fluoro4-methoxyphenyl)-3-(difluoromethyl)-1H-pyrazol-1-yl]benzenesulfonamide;
r6) 3-[1-[4-(methylsulfonyl)phenyl]4-trifluoromethyl-1H-imidazol-2-yl]pyridine;
r7) 2-methyl-5-[1-[4-(methylsulfonyl)phenyl]4-trifluoromethyl-1H-imidazol-2-yl]pyridine;
r8) 4-[2-(5-methylpyridin-3-yl)-4-(trifluoromethyl)-1H-imidazol-1-yl]benzenesulfonamide;
r9) 4-[5-methyl-3-phenylisoxazol4-yl]benzenesulfonamide;
r10) 4-[5-hydroxymethyl-3-phenylisoxazol4-yl]benzenesulfonamide;
s1) [2-trifluoromethyl-5-(3,4-difluorophenyl)4-oxazolyl]benzenesulfonamide;
s2) 4-[2-methyl-4-phenyl-5-oxazolyl]benzenesulfonamide; or
s3) 4-[5-(3-fluoro-4-methoxyphenyl-2-trifluoromethyl)-4-oxazolyl]benzenesulfonamide;
or a pharmaceutically acceptable salt or prodrug thereof.

In a further preferred embodiment of the invention the cyclooxygenase inhibitor can be selected from the class of tricyclic COX-2 inhibitors represented by the general structure of Formula IV:

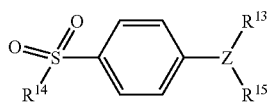

IV wherein:

Z is selected from the group consisting of partially unsaturated or unsaturated heterocyclyl and partially unsaturated or unsaturated carbocyclic rings;

$R^{13}$ is selected from the group consisting of heterocyclyl, cycloalkyl, cycloalkenyl and aryl, wherein $R^{13}$ is optionally substituted at a substitutable position with one or more radicals selected from alkyl, haloalkyl, cyano, carboxyl, alkoxycarbonyl, hydroxyl, hydroxyalkyl, haloalkoxy, amino, alkylamino, arylamino, nitro, alkoxyalkyl, alkylsulfinyl, halo, alkoxy and alkylthio;

$R^{14}$ is selected from the group consisting of methyl or amino; and $R^{15}$ is selected from the group consisting of a radical selected from H, halo, alkyl, alkenyl, alkynyl, oxo, cyano, carboxyl, cyanoalkyl, heterocyclyloxy, alkyloxy, alkylthio, alkylcarbonyl, cycloalkyl, aryl, haloalkyl, heterocyclyl, cycloalkenyl, aralkyl, heterocyclylalkyl, acyl, alkylthioalkyl, hydroxyalkyl, alkoxycarbonyl, arylcarbonyl, aralkylcarbonyl, aralkenyl, alkoxyalkyl, arylthioalkyl, aryloxyalkyl, aralkylthioalkyl, aralkoxyalkyl, alkoxyaralkoxyalkyl, alkoxycarbonylalkyl, aminocarbonyl, aminocarbonylalkyl, alkylaminocarbonyl, N-arylaminocarbonyl, N-alkyl-N-arylaminocarbonyl, alkylaminocarbonylalkyl, carboxyalkyl, alkylamino, N-arylamino, N-aralkylamino, N-alkyl-N-aralkylamino, N-alkyl-N-arylamino, aminoalkyl, alkylaminoalkyl, N-arylaminoalkyl, N-aralkylaminoalkyl, N-alkyl-N-aralkylaminoalkyl, N-alkyl-N-arylaminoalkyl, aryloxy, aralkoxy, arylthio, aralkylthio, alkylsulfinyl, alkylsulfonyl, aminosulfonyl, alkylaminosulfonyl, N-arylaminosulfonyl, arylsulfonyl, N-alkyl-N-arylaminosulfonyl;

or a prodrug thereof.

In a preferred embodiment of the invention the COX-2 inhibitor represented by the above Formula IV is selected from the group of compounds, illustrated in Table 2, which includes celecoxib (B-18), valdecoxib (B-19), deracoxib (B-20), rofecoxib (B-21), etoricoxib (MK-663; B-22), JTE-522 (B-23), or a prodrug thereof.

Additional information about selected examples of the COX-2 inhibitors discussed above can be found as follows: celecoxib (CAS RN 169590-42-5, C-2779, SC-58653, and in U.S. Pat. No. 5,466,823); deracoxib (CAS RN 169590-41-4); rofecoxib (CAS RN 162011-90-7); compound B-24 (U.S. Pat. No. 5,840,924); compound B-26 (WO 00/25779); and etoricoxib (CAS RN 202409-334, MK-663, SC-86218, and in WO 98/03484).

TABLE 2

Examples of Tricyclic Cox-2 Inhibitors as Embodiments

| Compound Number | Structural Formula |
|---|---|
| B-18 | (celecoxib structure) |
| B-19 | (valdecoxib structure) |
| B-20 | (deracoxib structure) |
| B-21 | (rofecoxib structure) |
| B-22 | (etoricoxib structure) |
| B-23 | (JTE-522 structure) |

In a more preferred embodiment of the invention, the COX-2 inhibitor is selected from the group consisting of celecoxib, rofecoxib and etoricoxib. In a preferred embodiment of the invention, parecoxib (U.S. Pat. No. 5,932,598), having the structure shown in B-24, which is a therapeutically effective prod rug of the tricyclic COX-2 inhibitor valdecoxib, B-19, (U.S. Pat. No. 5,633,272), may be advantageously employed as a source of a cyclooxygenase inhibitor. A preferred form of parecoxib is sodium parecoxib.

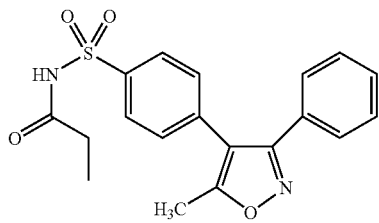
B-24

In another preferred embodiment of the invention, the compound ABT-963 having the formula B-25 that has been previously described in International Publication number WO 00/24719, is another tricyclic COX-2 inhibitor which may be advantageously employed.

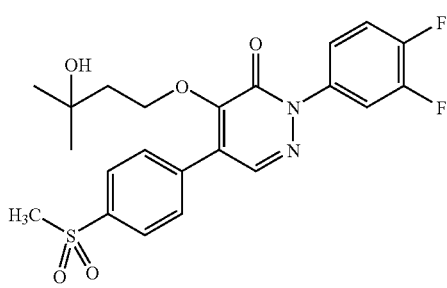
B-25

In a further preferred embodiment of the invention the cyclooxygenase inhibitor can be selected from the class of phenylacetic acid derivative COX-2 inhibitors represented by the general structure of Formula V:

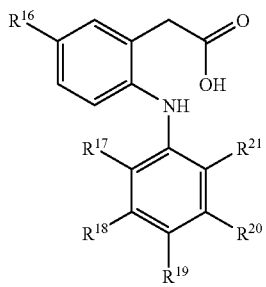
V wherein $R^{16}$ is methyl or ethyl;
$R^{17}$ is chloro or fluoro;
$R^{18}$ is hydrogen or fluoro;
$R^{19}$ is hydrogen, fluoro, chloro, methyl, ethyl, methoxy, ethoxy or hydroxy;
$R^{20}$ is hydrogen or fluoro; and
$R^{21}$ is chloro, fluoro, trifluoromethyl or methyl, provided that $R^{17}$, $R^{18}$, $R^{19}$ and $R^{20}$ are not all fluoro when $R^{16}$ is ethyl and $R^{19}$ is H.

A particularly preferred phenylacetic acid derivative COX-2 inhibitor that is described in WO 99/11605 is a compound that has the designation of COX189 (CAS RN 346670-74-4), and that has the structure shown in Formula V,
wherein $R^{16}$ is ethyl;
$R^{17}$ and $R^{19}$ are chloro;
$R^{18}$ and $R^{20}$ are hydrogen; and
$R^{21}$ is methyl.

Compounds that have a structure similar to that shown in Formula V, which can serve as the COX-2 inhibitor of the present invention, are described in U.S. Pat. Nos. 6,310,099 and 6,291,523.

Other preferred COX-2 inhibitors that can be used in the present invention have the general structure shown in formula VI, where the J group is a carbocycle or a heterocycle. Particularly preferred embodiments have the structure:

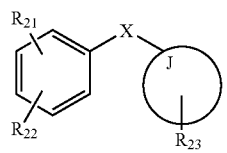
VI where:
X is O; J is 1-phenyl; $R_{21}$ is 2-NHSO$_2$CH$_3$; $R_{22}$ is 4-NO$_2$; and there is no $R_{23}$ group, (nimesulide); and
X is O; J is 1-oxo-inden-5-yl; $R_{21}$ is 2-F; $R_{22}$ is 4-F; and $R_{23}$ is 6-NHSO$_2$CH$_3$, (flosulide); and
X is O; J is cyclohexyl; $R_{21}$ is 2-NHSO$_2$CH$_3$; $R_{22}$ is 5-NO$_2$; and there is no $R_{23}$ group, (NS-398); and
X is S; J is 1-oxo-inden-5-yl; $R_{21}$ is 2-F; $R_{22}$ is 4-F; and $R_{23}$ is 6-N$^-$SO$_2$CH$_3$.Na$^+$, (L-745337); and
X is S; J is thiophen-2-yl; $R_{21}$ is 4-F; there is no $R_{22}$ group; and $R_{23}$ is 5-NHSO$_2$CH$_3$, (RWJ-63556); and
X is O; J is 2-oxo-5(R)-methyl-5-(2,2,2-trifluoroethyl)furan-(5H)-3-yl; $R_{21}$ is 3-F; $R_{22}$ is 4-F; and $R_{23}$ is 4-(p-SO$_2$CH$_3$) C$_6$H$_4$, (L-784512).

Further information on the applications of N-(2-cyclohexyloxynitrophenyl)methane sulfonamide (NS-398, CAS RN 123653-11-2), having a structure as shown in formula B-26, have been described by, for example, Yoshimi, N. et al., in *Japanese J. Cancer Res.*, 90(4):406-412 (1999); Falgueyret, J.-P. et al., in *Science Spectra*, available at: http://www.g-bhap.com/Science_Spectra/20-1-article.htm (May 6, 2001); and Iwata, K. et al., in *Jpn. J. Pharmacol.*, 75(2):191-194 (1997).

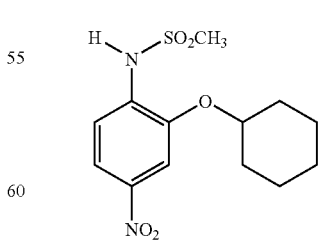
B-26

An evaluation of the antiinflammatory activity of the COX-2 inhibitor, RWJ 63556, in a canine model of inflammation, was described by Kirchner et al., in *J Pharmacol Exp Ther* 282, 1094-1101 (1997).

Other materials that can serve as he COX-2 inhibitor of the present invention include diarylmethylidenefuran derivatives that are described in U.S. Pat. No. 6,180,651. Such diarylmethylidenefuran derivatives have the general formula shown below in formula VII:

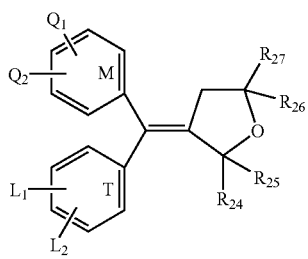

VII wherein:
the rings T and M independently are:
a phenyl radical,
a naphthyl radical,
a radical derived from a heterocycle comprising 5 to 6 members and possessing from 1 to 4 heteroatoms, or
a radical derived from a saturated hydrocarbon ring having from 3 to 7 carbon atoms;
at least one of the substituents $Q_1$, $Q_2$, $L_1$ or $L_2$ is:
an —$S(O)_n$—R group, in which n is an integer equal to 0, 1 or 2 and R is
a lower alkyl radical having 1 to 6 carbon atoms, or
a lower haloalkyl radical having 1 to 6 carbon atoms, or
an —$SO_2NH_2$ group;
and is located in the para position,
the others independently being:
a hydrogen atom,
a halogen atom,
a lower alkyl radical having 1 to 6 carbon atoms,
a trifluoromethyl radical, or
a lower O-alkyl radical having 1 to 6 carbon atoms, or
$Q_1$ and $Q_2$ or $L_1$ and $L_2$ are a methylenedioxy group; and
$R_{24}$, $R_{25}$, $R_{26}$ and $R_{27}$ independently are:
a hydrogen atom,
a halogen atom,
a lower alkyl radical having 1 to 6 carbon atoms,
a lower haloalkyl radical having 1 to 6 carbon atoms, or
an aromatic radical selected from the group consisting of phenyl, naphthyl, thienyl, furyl and pyridyl; or,
$R_{24}$, $R_{25}$ or $R_{26}$, $R_{27}$ are an oxygen atom, or
$R_{24}$, $R_{25}$ or $R_{26}$, $R_{27}$, together with the carbon atom to which they are attached, form a saturated hydrocarbon ring having from 3 to 7 carbon atoms;
or an isomer or prodrug thereof.

Particular materials that are included in this family of compounds, and which can serve as the COX-2 inhibitor in the present invention, include N-(2-cyclohexyloxynitrophenyl) methane sulfonamide, and (E)-4-[(4-methylphenyl)(tetrahydro-2-oxo-3-furanylidene) methyl]benzenesulfonamide.

COX-2 inhibitors that are useful in the present invention include darbufelone (Pfizer), CS-502 (Sankyo), LAS 34475 (Almirall Profesfarma), LAS 34555 (Almirall Profesfarma), S-33516 (Servier, see *Current Drugs Headline News*, at http://www.current-drugs.com/NEWS/lnflam1.htm, Oct. 4, 2001), BMS-347070 (Bristol Myers Squibb, described in U.S. Pat. No. 6,180,651), MK-966 (Merck), L-783003 (Merck), T-614 (Toyama), D-1367 (Chiroscience), L-748731 (Merck), CT3 (Atlantic Pharmaceutical), CGP-28238 (Novartis), BF-389 (Biofor/Scherer), GR-253035 (Glaxo Wellcome), 6-dioxo-9H-purin-8-yl-cinnamic acid (Glaxo Wellcome), and S-2474 (Shionogi).

COX-2 inhibitors that are useful in the invention can include the compounds that are described in U.S. Pat. Nos. 6,310,079; 6,306,890 and 6,303,628 (bicycliccarbonyl indoles); U.S. Pat. No. 6,300,363 (indole compounds); U.S. Pat. Nos. 6,297,282 and 6,004,948 (substituted derivatives of benzosulphonamides); U.S. Pat. Nos. 6,239,173, 6,169,188, 6,133,292; 6,020,343; 6,071,954; 5,981,576 ((methylsulfonyl)phenyl furanones); U.S. Pat. No. 6,083,969 (diarylcycloalkano and cycloalkeno pyrazoles); U.S. Pat. No. 6,222,048 (diaryl-2-(5H)-furanones; U.S. Pat. No. 6,077,869 (aryl phenylhydrazines); U.S. Pat. Nos. 6,071,936 and 6,001,843 (substituted pyridines); U.S. Pat. No. 6,307,047 (pyridazinone compounds); U.S. Pat. No. 6,140,515 (3-aryl-4-aryloxyfuran-5-ones); U.S. Pat. Nos. 6,204,387 and 6,127,545 (diaryl pyridines); U.S. Pat. No. 6,057,319 (3,4-diaryl-2-hydroxy-2,5-dihydrofurans; U.S. Pat. No. 6,046,236 (carbocyclic sulfonamides); and U.S. Pat. Nos. 6,002,014; 5,994,381; and 5,945,539 (oxazole derivatives).

In an embodiment of the present method, a subject in need of prevention, treatment or inhibition of a psychiatric disorder is treated with a COX-2 inhibitor or prodrug thereof. In particular the subject is treated with an effective amount of the COX-2 inhibitor, whereby the effective amount can be a therapeutic amount, and it can be an amount that is an effective amount for the prevention, treatment or inhibition of a psychiatric disorder.

As used herein, an "effective amount" means the dose or effective amount to be administered to a patient and the frequency of administration to the subject which is readily determined by one or ordinary skill in the art, by the use of known techniques and by observing results obtained under analogous circumstances. The dose or effective amount to be administered to a patient and the frequency of administration to the subject can be readily determined by one of ordinary skill in the art by the use of known techniques and by observing results obtained under analogous circumstances. In determining the effective amount or dose, a number of factors are considered by the attending diagnostician, including but not limited to, the potency and duration of action of the compounds used; the nature and severity of the illness to be treated as well as on the sex, age, weight, general health and individual responsiveness of the patient to be treated, and other relevant circumstances.

The phrase "therapeutically-effective" indicates the capability of an agent to prevent, or improve the severity of, the disorder, while avoiding adverse side effects typically associated with alternative therapies. The phrase "therapeutically-effective" is to be understood to be equivalent to the phrase "effective for the treatment, prevention, or inhibition", and both are intended to qualify the amount of each agent for use in the combination therapy which will achieve the goal of improvement in the severity of neurological or psychiatric disorder and the frequency of incidence over treatment of each agent by itself, while avoiding adverse side effects typically associated with alternative therapies. Accordingly, a "therapeutic amount", or a "therapeutically effective amount" of a medication is an amount that is therapeutically effective. Those skilled in the art will appreciate that dosages may also be determined with guidance from Goodman & Goldman's *The Pharmacological Basis of Therapeutics*, Ninth Edition (1996), Appendix II, pp.1707-1711.

Preferred COX-2 inhibitors for the method of the present invention include celecoxib (Celebrex®), rofecoxib (Vioxx®), meloxicam, piroxicam, deracoxib, parecoxib, valdecoxib, etoricoxib, a chromene derivative, a chroman derivative, N-(2-cyclohexyloxynitrophenyl)methane sulfonamide, COX189, ABT963, JTE-522, pharmaceutically acceptable salts, prodrugs or mixtures thereof. More preferred COX-2 inhibitors are celecoxib, parecoxib, valdecoxib, etoricoxib and rofecoxib.

According to a preferred embodiment of the method of the present invention, celecoxib (Celebrex®) or a pharmaceutically acceptable salt thereof is used. The term pharmaceutically acceptable salt includes salts that can be prepared according to known methods by those skilled in the art from the corresponding compound of the present invention, e.g. conventional metallic ion salts and organic salts.

Celecoxib can be administered at a dose of 50-1600 mg per day, preferably 200 to 600 mg, most preferably 400 mg per day. The administration can be carried out once or several times a day, preferably twice. The amount of celecoxib can be adapted depending on age, body weight and/or possible other diseases of the patient. Preferably, celecoxib is used in the form of tablets (Celebrex®) for oral administration.

Without intending to establish a certain theory as explanation for the observed effect of COX-2 inhibitors, the following mechanisms of action are taken into consideration.

There is no doubt that activation of COX-2 mediates inflammatory processes and that COX-2 is expressed in brain tissue. COX-2 can be activated by cytokines like IL-2, IL-6 and IL-10, and cytokine-activated COX-2 expression mediates further inflammatory processes. It was reported that IL-2 and soluble IL-2 receptors (Licino J, Seibyl, J P, Altemus M, Charney D S, Krystal J H: Elevated levels of Interleukin-2 in neuroleptic-free schizophrenics. Am J Psychiatry 1993; 150: 1408-1410) (McAllister C G, van Kemmen D P, Rehn T J, Miller A L, Gurklis J, Kelley M E, Yao J, Peters J L: Increases in CSF levels of Interleukin-2 in schizophrenia: effects of recurrence of psychosis and medication status. Am J Psychiatry 1995; 152: 1291-1297), soluble IL-6 receptors as a functional part of the IL-6 system (Müller N, Dobmeier P, Empel M, Riedel M, Schwarz M, Ackenheil M: Soluble IL-6 Receptors in the serum and cerebrospinal fluid of paranoid schizophrenic patients. Eur Psychiatry 1997; 12: 294-299) and IL-10 (Van Kammen D P, McAllister-Sistilli C G, Kelley M E: Relationship between immune and behavioral measures in schizophrenia. In: G. Wieselmann (ed.) Current Update in Psychoimmunology, Springer Verlag 1997; Wien, NY, pp. 51-55) are increased in the cerebrospinal fluid of schizophrenic patients—the increase of the cytokines in the CNS may be accompanied by increased COX-2 expression. The effectiveness of COX-2 inhibitors, such as celecoxib, in the treatment of schizophrenia, might be based on the finding that celecoxib down-regulates the cytokine-induced CNS COX-2 activation.

Moreover, COX-2 inhibition seems to regulate the expression of adhesion molecules (Schwarz M J, Ackenheil M, Riedel M, Müller N: Blood-CSF-Barrier impairment as indicator for an immune process in schizophrenia. Neurosci Letters 1998; 253: 201-203). Since adhesion molecule regulation is impaired in schizophrenia, leading to dysbalance and lack of communication between the peripheral and the CNS immune system, the effects of COX-2 inhibitors, such as celecoxib, in the treatment of schizophrenia, may also be related to the adhesion molecules ICAM-1 and VCAM-1, expecially regarding the negative symptoms (Schwarz M J, Riedel M, Gruber R, Ackenheil M, Müller N: Levels of soluble adhesion molecules in schizophrenia: Relation to psychopathology. In: N. Muller (Hrg) Psychiatry, Psychoneuroimmunology, and Viruses. Springer Verlag Wien, 1999, NY, pp. 121-130; Müller N, Ackenheil M: Immunoglobulin and albumin contents of cerebrospinal fluid in schizophrenic patients: The relationship to negative sympomatology. Schizophrenia Res 1995; 14: 223-228).

According to a further embodiment of the present invention, a method and composition for the prevention, treatment or inhibition of psychiatric disorders comprising administering COX-2 inhibitor in combination with a neuroleptic drug or an antidepressant are provided. The psychiatric disorders include schizophrenia, delusional disorders, affective disorders, autism and tic disorders, in particular chronic schizophrenic psychoses and schizoaffective psychoses, temporary acute psychotic disorders, depressive episodes, recurring depressive episodes, manic episodes and bipolar affective disorders. Combinations can also include a mixture of one or more COX-2 inhibitors with one or more neuroleptic agents or antidepressant. In particular, the combination of a COX-2 inhibitor with a neuroleptic drug is useful for the treatment of schizophrenia, whereas the combination of a COX-2 inhibitor with an antidepressant is applicable for the treatment of depressive disorders.

Both classical and atypical neuroleptics can be used for the add-on use according to the invention, atypical neuroleptics being preferred.

Examples of neuroleptic drugs that are useful in the present invention include, but are not limited to: butyrophenones, such as haloperidol, pimozide, and droperidol; phenothiazines, such as chlorpromazine, thioridazine, mesoridazine, trifluoperazine, perphenazine, fluphenazine, thiflupromazine, prochlorperazine, and acetophenazine; thioxanthenes, such as thiothixene and chlorprothixene; thienobenzodiazepines; dibenzodiazepines; benzisoxazoles; dibenzothiazepines; imidazolidinones; benzisothiazolyl-piperazines; dibenzoxazepines, such as loxapine; dihydroindolones, such as molindone; aripiprazole; and derivatives thereof that have antipsychotic activity.

Examples of neuroleptic drugs that are preferred for use in the present invention are shown in Table 3.

TABLE 3

| Neuroleptic drugs | | | | |
|---|---|---|---|---|
| Common Name | Trade Name | Route of Administration | Form | Dosage Range and (Median)[a] |
| Clozapine | CLOZARIL | oral | tablets | 12.5-900 mg/day (300-900 mg/day) |
| Olanzapine | ZYPREXA | oral | tablets | 5-25 mg/day (10-25 mg/day) |

TABLE 3-continued

Neuroleptic drugs

| Common Name | Trade Name | Route of Administration | Form | Dosage Range and (Median)[a] |
|---|---|---|---|---|
| Ziprasidone | GEODON | oral | capsules | 20-80 mg/twice a day (80-160 mg/day) |
| Risperidone | RISPERDAL | oral | solution tablets | 2-16 mg/day (4-12 mg/day) |
| Quetiapine fumarate | SEROQUEL | oral | tablets | 50-900 mg/day (300-900 mg/day) |
| Sertindole | SERLECT | | | (4-24 mg/day) |
| Amisulpride | | | | |
| Haloperidol | HALDOL | oral | tablets | 1-100 mg/day (1-15 mg/day) |
| Haloperidol Decanoate | HALDOL Decanoate | parenteral | injection | |
| Haloperidol lactate | HALDOL INTENSOL | oral | solution | |
| | | parenteral | injection | |
| Chlorpromazine | THORAZINE | rectal | suppositories | 30-800 mg/day (200-500 mg/day) |
| | | oral | capsules solution tablets | |
| | | parenteral | injection | |
| Fluphenazine | PROLIXIN | | | 0.5-40 mg/day (1-5 mg/day) |
| Fluphenazine decanoate | PROLIXIN Decanoate | parenteral | injection | (about one-half the dosage shown for oral) |
| Fluphenazine enanthate | PROLIXIN | parenteral | injection | (same as above) |
| Fluphenazine hydrochloride | PROLIXIN | oral | elixer solution tablets | |
| | | parenteral | injection | |
| Thiothixene | NAVANE | oral | capsules | 6-60 mg/day (8-30 mg/day) |
| Thiothixene hydrochloride | NAVANE | oral | solution | |
| | | parenteral | injection | |
| Trifluoperazine | STELAZINE | | | (2-40 mg/day) |
| Perphenazine | TRILAFON | oral | solution tablets | 12-64 mg/day (16-64 mg/day) |
| | | parenteral | injection | |
| Perpehazine and Amitriptyline hydrochloride | ETRAFON TRIAVIL | oral | tablets | |
| Thioridazine | MELLARIL | oral | suspension solution tablets | 150-800 mg/day (100-300 mg/day) |
| Mesoridazine | | | | (30-400 mg/day) |
| Molindone | MOBAN | | | 50-225 mg/day (15-150 mg/day) |

TABLE 3-continued

Neuroleptic drugs

| Common Name | Trade Name | Route of Administration | Form | Dosage Range and (Median)[a] |
|---|---|---|---|---|
| Molindone hydrochloride | MOBAN | oral | solution | |
| Loxapine | LOXITANE | | | 20-250 mg/day (60-100 mg/day) |
| Loxapine hydrochloride | LOXITANE | oral | solution | |
| Loxapine succinate | LOXITANE | parenteral oral | injection capsules | |
| Pimozide | | | | (1-10 mg/day) |
| Flupenthixol | | | | |
| Promazine | SPARINE | | | |
| Triflupromazine | VESPRIN | | | |
| Chlorprothixene | TARACTAN | | | |
| Droperidol | INAPSINE | | | |
| Acetophenazine | TINDAL | | | |
| Prochlorperazine | COMPAZINE | | | |
| Methotrimeprazine | NOZINAN | | | |
| Pipotiazine | PIPOTRIL | | | |
| Ziprasidone | | | | |
| Hoperidone | | | | |
| Zuclopenthixol | | | | |

Examples of tradenames and suppliers of selected neuroleptic drugs are as follows: clozapine (available under the tradename CLOZARIL®, from Mylan, Zenith Goldline, UDL, Novartis); olanzapine (available under the tradename ZYPREXA®, from Lilly;

ziprasidone (available under the tradename GEODON®, from Pfizer); risperidone (available under the tradename RISPERDAL®, from Janssen); quetiapine fumarate (available under the tradename SEROQUEL®, from AstraZeneca); haloperidol (available under the tradename HALDOL®, from Ortho-McNeil); chlorpromazine (available under the tradename THORAZINE®, from SmithKline Beecham); fluphenazine (available under the tradename PROLIXIN®, from Apothecon, Copley, Schering, Teva, and American Pharmaceutical Partners, Pasadena); thiothixene (available under the tradename NAVANE®, from Pfizer); trifluoperazine (10-[3-(4-methyl-1-piperazinyl) propyl]-2-(trifluoromethyl) phenothiazine dihydrochloride, available under the tradename STELAZINE®, from SmithKlein Beckman); perphenazine (available under the tradename TRILAFON®, from Schering);

thioridazine (available under the tradename MELLARIL®, from Novartis, Roxane, Hi-Tech, Teva, and Alpharma); molindone (available under the tradename MOBAN®, from Endo); and loxapine (available under the tradename LOXITANE® from Watson). Furthermore, benperidol (Glianimon®), perazine (Taxilan®) or melperone (Eunerpan®) may be used.

Other preferred neuroleptic drugs include promazine (available under the tradename SPARINE®), triflurpromazine (available under the tradename VESPRIN®), chlorprothixene (available under the tradename TARACTAN®), droperidol (available under the tradename INAPSINE®), acetophenazine (available under the tradename TINDAL®), prochlorperazine (available under the tradename COMPAZINE®), methotrimeprazine (available under the tradename NOZINAN®), pipotiazine (available under the tradename PIPOTRIL®), ziprasidone, and hoperidone.

Preferred neuroleptic drugs include risperidone and aripiprazole (from Bristol Myers Squibb Company, see e.g. Stahl S M; Dopamine-system stabilizers, aripiprazole and the next generation of antipsychotics, part I, "goldilocks"-actions at dopamine receptors; J. Clin. Psychiatry 2001, 62, 11:841-842).

The most preferred neuroleptic drug within the present invention is risperidone (Risperdal®), its manufacture and pharmacological activity is described in EP 0 196 132. Risperidone acts as an antagonist to neurotransmitters, in particular dopamine, and is used for the treatment of psychoses.

Various types of antidepressants can be used for the add-on use according to the present invention. Examples of antidepressants that are useful in the present invention include, but are not limited to: tricyclic antidepressants such as amitriptyline (5-(3-dimethylamino propylidene)-10,11-dihydro-5H-dibenzo[a,d]cyclohepten), amitriptyline oxide, desipramine (10,11-dihydro-5-(3-methylamino propyl)-5H-dibenz[b,f]azepin), dibenzepin (10-(2-dimethylamino ethyl)-5,11-dihydro-5-methyl-11H-dibenzo[b,e][1,4]diazepin-11-on), dosulepin (3-(6H-dibenzo[b,e]thiepin-11-yliden)-N,N-dimethylpropyl amine), doxepin (3-(6H-dibenz[b,e]oxepin-11-yliden)-dimethylpropyl amine), chloroimipramine, imipramine (5-(3-dimethylamino propyl)-5,11-dihydro-5H-dibenz[b,f]azepin), nortriptyline (3-(10,11-dihydro-5H-dibenzo[a,d]cyclohepten-5-yliden)-N-methyl-1-propane amine), mianserin (1,2,3,4,10,14b-hexahydro-2-methyl-dibenzo[c,f]pyrazino[1,2-a]azepin), maprotiline (N-methyl-9,10-ethanoanthracene-9(10H)-propane amine), trimipramine (5-[3-dimethylamino)-2-methylpropyl]-10,11-dihydro-5H-dibenz[b,f]-azepin) or viloxazine (RS)-2-(2-ethyoxy phenoxy methyl)-morpholine), modern antidepressants such as trazodone (2-{3-[4-(3-chlorophenyl)-1-piperazinyl]-propyl}-1,2,4-triazolo[4,3-a]pyridine-3 (2H)-on, nefazodone (2-{3-[4-(3-chlorophenyl)-1-piperazinyl]propyl}-5-ethyl-2,4-dihydro-4-(2-phenoxyethyl)-3H-1, 2,4-triazol-3-on), mirtazapine ((±)-1,2,3,4,10,14b-hexahydro-2-methylpyrazino[2,1-a]pyrido[2,3-c][2]

benzazepin), venlafaxine ((±)-1-2-(dimethylamino)-1-(4-methoxyphenyl)-ethyl]cyclohexanol) or reboxetine ((±)-(2RS)-2-[(α SR)-α-(2-ethoxyphenoxy)benzyl]morpholine), inhibitors of monoaminooxidases such as tranylcypromine (trans-2-phenyl cyclopropyl amine), brofaromine or moclobemide (4-chloro-N-(2-morpholinoethyl)-benzamide), selective inhibitors of serotonin-uptake such as citalopram, paroxetine, fluoxetine ((RS)—N-methyl-3-phenyl-3-[4-(trifluoromethyl)phenoxy]propyl amine, available under the tradename PROZAC®), fluvoxamine ((E)-5-methyoxy-4'-(trifluoromethyl)-valerophenon-O-(2-aminoethyl) oxime) or sertraline ((1 S-cis)-(+)-4-(3,4-dichlorophenyl)-1,2,3,4-tetrahydro-N-methyl-1-naphthalinamine), and vegetable antidepressants such as Hypericum (St. John's wort).

In the present method, the subject is treated with an amount of a neuroleptic agent or antidepressant and an amount of a COX-2 inhibitor, where the amount of the neuroleptic agent or antidepressant and the amount of the COX-2 inhibitor together provide a dosage or amount of the combination that is sufficient to constitute an effective amount of the combination. The effective amount can be a therapeutic amount, and it can be an amount that is an effective amount for the prevention, treatment or inhibition of a psychiatric disorder. In the present method, the amount of the neuroleptic agent or antidepressant that is used is such that, when administered with the COX-2 inhibitor, it is sufficient to constitute an effective amount of the combination. It is preferred that the dosage amount of the neuroleptic agent or 2o antidepressant and the dosage amount of the COX-2 inhibitor constitute a therapeutically effective amount of the combination of the two.

It is well known that different neuroleptic agents or antidepressant have different levels of potency and that recommended dosage levels vary considerably. The recommended dosage level for a commercial neuroleptic agent or antidepressant can be found in the prescribing information that is published by the distributor. Some allowable and preferred dosage levels for selected neuroleptic agents that are preferred for use in the present invention are shown in Table 3.

According to a preferred embodiment of present method and composition, the neuroleptic risperidone is administered at a dose of 2-6 mg/day, preferably 4-5 mg.

The dose for celecoxib may range from 50-1600 mg/day, preferably 200-600, more preferably 400 mg. Preferably, the administration occurs twice daily (in the morning and in the evening).

The frequency of dose will depend upon the half-life of the neuroleptic agent or antidepressant molecule. If the molecule has a short half life (e.g. from about 2 to 10 hours) it may be necessary to give one or more doses per day. Alternatively, if the molecule has a long half-life (e.g. from about 2 to about 15 days) it may only be necessary to give a dosage once per day, per week, or even once every 1 or 2 months. A preferred dosage rate is to administer the dosage amounts described above to a subject once or twice per day. The amount of Cox-2 selective inhibitor that is used in the subject method may be an amount that, when administered with the neuroleptic agent or antidepressant, is sufficient to constitute an effective amount of the combination. Preferably, such amount would be sufficient to provide a therapeutically effective amount of the combination.

In the present method, and in the subject compositions, the neuroleptic agent or antidepressant is administered with, or is combined with, a COX-2 inhibitor.

The combination of a neuroleptic agent and a COX-2 inhibitor, or of an antidepressant and a COX-2 inhibitor, can be supplied in the form of a novel therapeutic composition that is believed to be within the scope of the present invention. The relative amounts of each component in the therapeutic composition may be varied. The COX-2 inhibitors and the neuroleptic agents or antidepressants can be provided in the therapeutic composition so that the preferred amounts of each of the components are supplied by a single dosage, a single injection or a single capsule for example, or, by up to four, or more, single dosage forms.

Any one or more of the COX-2 inhibitors that are described above can be combined with any one or more of the neuroleptic agents ore antidepressants that are described above in the novel method and combinations of the present invention. By way of example, combinations can include a Cox-2 selective inhibitor, such as celecoxib, rofecoxib, parecoxib, valdecoxib, etoricoxib, deracoxib, and NS-398, and a neuroleptic agent, such as clozapine, olanzapine, ziprasidone, risperidone, quetiapine, quetiapine fumarate, sertindole, amisulpride, haloperidol, haloperidol decanoate, haloperidol lactate, chlorpromazine, fluphenazine, fluphenazine decanoate, fluphenazine enanthate, fluphenazine hydrochloride, thiothixene, thiothixene hydrochloride, trifluoperazine, perphenazine, amitriptyline, thioridazine, mesoridazine, molindone, molindone hydrochloride, loxapine, loxapine hydrochloride, loxapine succinate, pimozide, flupenthixol, promazine, triflupromazine, chlorprothixene, droperidol, actophenazine, prochlorperazine, methotrimeprazine, pipotiazine, ziprasidone, hoperidone and zuclopenthixol. Combinations can also include a mixture of one or more Cox-2 selective inhibitors with one or more neuroleptic agents.

When the novel combination is supplied along with a pharmaceutically acceptable carrier, a pharmaceutical composition is formed. The pharmaceutical composition comprises a pharmaceutically acceptable carrier, a neuroleptic agent or antidepressant, and a COX-2 inhibitor. Pharmaceutically acceptable carriers include, but are not limited to, physiological saline, Ringer's, phosphate solution or buffer, buffered saline, and other carriers known in the art. Pharmaceutical compositions may also include stabilizers, anti-oxidants, colorants, and diluents. Pharmaceutically acceptable carriers and additives are chosen such that side effects from the pharmaceutical compound are minimized and the performance of the compound is not canceled or inhibited to such an extent that treatment is ineffective.

The invention is also directed to a novel kit that is suitable for use in the treatment of psychiatric disorders such as schizophrenia, delusional disorders, affective disorders, autism or tic disorders, comprising a first dosage form comprising a neuroleptic agent or antidepressant and a second dosage form comprising a COX-2 inhibitor or prodrug thereof, in quantities which comprise a therapeutically effective amount of the combination of the compounds for the treatment, prevention, or inhibition of a psychiatric disorder, for simultaneous, separate or sequential administration.

According to a preferred embodiment, the dosage form comprising a neuroleptic agent or antidepressant and the second dosage form comprising a COX-2 inhibitor are administered simultaneously. Examples for COX-inhibitors and neuroleptics or antidepressants usable in the kit-of-parts of the present invention are listed above with reference to methods or compositions of the present invention.

The subject pharmaceutical kit may be administered enterally (orally) or parenterally. Parenteral administration includes subcutaneous, intramuscular, intradermal, intramammary, intravenous, and other administrative methods known in the art. Enteral administration includes solution, tablets, sustained release capsules, enteric coated capsules, and syrups. Preferably the administration of a pharmaceutical kit comprising a COX-2 inhibitor and a neuroleptic or antidepressant occurs enterally (orally), in form of tablets.

According to a preferred embodiment, the kit comprises celecoxib or a pharmaceutically acceptable salt thereof as COX-2 inhibitor and risperidone as neuroleptic drug. Most preferably, the celecoxib is comprised in an amount of 50-1600 mg, preferably 200-600 mg and most preferably 400 mg, and risperidone in an amount of 2-6 mg, preferably 4-5 mg.

The treatment of psychiatric disorders with COX-2 inhibitors, alone or in combination with a neuroleptic or antidepressant, may occur in addition to further drug therapies. Thus, tranquilizers may be used for the treatment of agitation, anxiety or sleep disturbances. Preferably lorazepam is used, which belongs to the class of benzodiazepines.

In the following, the invention will be discussed in more detail with reference to a patient study. Other embodiments within the scope of the claims herein will be apparent to one skilled in the art from consideration of the specification or practice of the invention as disclosed herein. The results of the patient study are graphically represented in the attached figures, which will be discussed in more detail in the following.

FIG. 1 shows the comparison of the PANSS score during treatment with risperidone-celecoxib or risperidone-placebo.

FIG. 2 shows the comparison of the PANSS negative score during treatment with risperidone-celecoxib or risperidone-placebo.

FIG. 3 shows the comparison of the PANSS global score during treatment with risperidone-celecoxib or risperidone-placebo.

FIG. 4 shows the plasma levels of risperidone and 9-OH-risperidone during treatment with risperidone-celecoxib or risperidone-placebo.

FIG. 5 shows the biperiden and benzodiazepine use during treatment with risperidone-celecoxib or risperidone-placebo.

The study was performed as a single-center, double-blind, placebo-controlled, 2 o randomized, parallel-groupe valuation of the combination therapy with celecoxib and risperidone versus a monotherapy with risperidone and placebo in schizophrenic patients. The study included 50 patients fulfilling the criteria for the diagnosis of schizophrenia according to DSM IV (American Psychiatric Association (1994), Diagnostic and Statistical Manual of Mental Disorders, 1 st Edition, American Psychiatric Press, Washington D.C.), of whom 25 belonged to the risperidone-placebo and 25 to the risperidone-celecoxib group. No significant differences were present between the two patient groups were found with regard to age, sex, duration or severity of the disease or psychopathology, risperidone dose or risperidone-plasma levels.

The patients received 2-6 mg/day of risperidone (Risperdal®), and depending on to which group they belonged, 400 mg/day of celecoxib (2×200 mg Celebrex® mornings and evenings) or placebo over 5 weeks after a brief wash-out period of earlier antipsychotic medication. During the wash-out period, a benzodiazepine preparation (mostly lorazepam) was prescribed, if necessary. Patients with agitation, anxiety, or sleeping problems were also medicated with lorazepam during the study.

The psychopathology of the patients was assessed using the positive and negative syndrome scale (PANSS) (Kay et al., Schizophr. Bull. 1987, 13:261-276).

The extrapyramidal side effects were assessed by the EPS scale (Simpson and Angus, Acta Psychiat. Scand. 1970 (Suppl.), 212). The use of biperiden was monitored as a possible indicator for side effects of the antipsychotic medication.

In order to exclude the chance that possible differences in the therapeutic effectiveness between the two groups might be due to non-compliance during the risperidone therapy or to differences in risperidone metabolism, the plasma levels of risperidone or 9-OH-risperidone were monitored during the study.

The statistics were performed according to the criterion of "last observation carried forward" (LOCF), i.e., the last PANSS scores of the patients who dropped out before the end of the study were carried forward to all subsequent observation days. For the comparison of the main efficacy parameter, the mean change in the PANSS between the two treatment groups, t-tests for independent samples were employed. With reference to the underlying hypothesis of a better outcome of the celecoxib-risperidone group, a significance of p<0.05 was calculated in the one-tailed t-test and used as the basis for the estimation of the sample size (statistical power) and for the comparison of the groups. For all other comparisons, two-tailed t-tests were used.

At the start of the study, in the risperidone-celecoxib group (average age 35.9±12.8 years), the PANSS total score was 71.8±17.1, the PANSS global score was 34.0±8.5, the PANSS positive score was 19.0±5.9 and the PANSS negative score was 18.7±6.3. In the risperidone-placebo group (average age 35.5±13.6 years), the PANSS total score was 75.4±12.9, the PANSS global score was 37.2±7.1, the PANSS positive score was 17.2±4.6 and the PANSS negative score was 21.1±5.5. Consequently, there was no significant difference in the PANSS total score or any of the subscales.

During the five-week therapy, a significant improvement of the PANSS total score and the subscales is observed in both groups of schizophrenic patients. The results of the PANSS total score are shown in FIG. 1, of the PANSS negative score in FIG. 2, of the PANSS global score in FIG. 3 and of the PANSS positive score in Table 4.

TABLE 4

Comparison of the PANSS positive score

| time | celecoxib and risperidone | placebo and risperidone | t[1] | p[2] |
|---|---|---|---|---|
| week 0 | 19.0 ± 5.9 | 17.2 ± 4.6 | 1.22 | n.s.[3] |
| week 1 | 16.7 ± 5.5 | 16.2 ± 4.6 | 0.36 | n.s. |
| week 2 | 14.4 ± 5.0 | 15 ± 4.5 | 0.42 | n.s. |
| week 3 | 14.0 ± 4.7 | 14.5 ± 4.6 | 0.36 | n.s. |
| week 4 | 12.8 ± 4.4 | 14.2 ± 4.4 | 1.16 | n.s. |
| week 5 | 13.4 ± 5.6 | 13.3 ± 4.4 | 0.11 | n.s. |

[1] t represents the statistical random sample distribution.
[2] p represents the statistical power (probability).
[3] n.s. means no statistical significance.

In the celecoxib-risperidone group, the two-tailed t-tests between the baseline and week 5 gave the following values: PAN SS total score p<0.0001, PAN SS global score p<0.0001, PANSS positive score p<0.0001, PAN SS negative score p<0.001. In the placebo-risperidone group, the t-tests between the baseline and week 5 gave the following values: PANSS total score p<0.002, PANSS global score p<0.003, PANSS positive score p<0.002, PANSS negative score p<0.02.

The improved effectiveness of the combination therapy with celecoxib-risperidone in comparison to risperidone monotherapy is clearly shown by the significantly lower PANSS global scores after the 2, 3, 4 and 5 weeks of treatment (FIG. 3). With regard to the total and negative score, significantly lower scores were recorded after 2, 3 and 4 weeks in the celecoxib-risperidone group (FIGS. 1 and 2).

The mean daily dose of risperidone is shown in Table 5; no statistically significant difference was found between the two treatment groups.

TABLE 5

Mean risperidone dose mg/day

| time | celecoxib and risperidone | placebo and risperidone | difference |
|---|---|---|---|
| week 1 | 4.1 ± 0.6 | 4.0 ± 0.8 | n.s. |
| week 2 | 4.5 ± 0.6 | 4.4 ± 1.1 | n.s. |
| week 3 | 4.8 ± 0.8 | 4.9 ± 1.4 | n.s. |
| week 4 | 5.0 ± 1.0 | 4.9 ± 1.4 | n.s. |
| week 5 | 4.9 ± 1.0 | 5.1 ± 1.5 | n.s. |

[1]n.s. means no statistical significance.

The differences in the plasma levels of risperidone or the metabolite 9-OH-risperidone shown in FIG. 4 were also without statistical significance (the present FIG. 4 differs from FIG. 4 of the German patent application priority document due to a calculation error in said priority document).

Therefore, it could be excluded that the observed differences in the therapeutic effectiveness between the two groups are due to incompatibility during the risperidone therapy or differences in risperidone metabolism. The therapeutic benefit of the combined therapy has to be attributed to the COX-2 inhibitor, celecoxib.

With respect to the extrapyramidal side effects, no statistically significant differences were found in the EPS scale. The use of biperiden is shown in FIG. 5 and was calculated as cumulative weekly dose. The values were lower in the celecoxib-risperidone group, and reached statistical significance at week 2 (p<0.02). A detailed analysis of items of the PANSS-Scale which discriminate good celecoxib-responders from the placebo group revealed that therapeutic effects of celecoxib are especially found on the items "lack of contact" (item 3 of the negative subscale), "emotional isolation" (item 2 of the negative subscale), "passive-apathic isolation" (item 4 of the negative subscale), "social withdrawal" (item 16 of the general psychopathology subscale), "depression" (item 6 of the general psychopathology subscale) and "motor retardation" (item 6 of the general psychopathology subscale).

Furthermore, a factor analysis showed that especially items which can subsumed under the label "agitation" show a good therapeutic response to celecoxib, but not to placebo. All those items reflect psychopathological symptoms which are typically found in depressive states. Therefore this detailed analysis points to a therapeutic efficiency in depressive states.

Moreover, "passive-apathic isolation", "motor retardation", "social withdrawal", or "lack of contact" are—often more severe expressed than in depressive states—also coresymptoms of childhood autism.

The combination of celecoxib and risperidone according to the present invention thus shows improved results compared to the monopreparation risperidone with regard to effectiveness in the treatment of schizophrenia. Furthermore, it was observed that the beneficial effects of the add-on therapy occurred faster in patients with a recent onset of the disorder and that the celecoxib therapy was useful in the treatment of depressive states.

As various changes could be made in the above methods and compositions without departing from the scope of the invention, it is intended that all matter contained in the above description shall be interpreted as illustrative and not in a limiting sense.

What is claimed is:

1. A method for the treatment of schizophrenia comprising administering to a subject in need an effective amount of a selective COX-2 inhibitor or prodrug thereof, wherein the selective COX-2 inhibitor is a selective COX-2 inhibitor of the following formula IV:

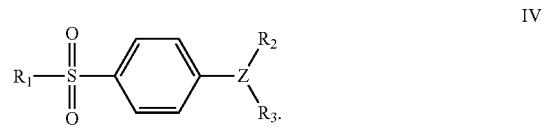

IV wherein

Z is selected from the group consisting of partially unsaturated or unsaturated heterocyclyl and partially unsaturated or unsaturated carbocyclic rings;

$R_1$ is selected from the group consisting of methyl or amino; and $R_2$ is selected from the group consisting of heterocyclyl, cycloalkyl, cycloalkenyl and aryl, wherein $R_2$ is optionally substituted at a substitutable position with one or more radicals selected from alkyl, haloalkyl, cyano, carboxyl, alkoxycarbonyl, hydroxyl, hydroxyalkyl, haloalkoxy, amino, alkylamino, arylamino, nitro, alkoxyalkyl, alkylsulfinyl, halo, alkoxy and alkylthio; and $R_3$ is selected from the group consisting of a radical selected from hydrogen, halogen, alkyl, alkenyl, alkynyl, oxygen, cyano, carboxyl, cyanoalkyl, alkyloxy, alkylthio, alkylcarbonyl, haloalkyl, alkylthioalkyl, hydroxyalkyl, alkoxycarbonyl, alkoxycarbonylalkyl, aminocarbonyl, aminocarbonylalkyl, alkylaminocarbonyl, alkylaminocarbonylalkyl, carboxyalkyl, alkylamino, aminoalkyl, alkylaminoalkyl, alkylsulfinyl, alkylsulfonyl, aminosulfonyl, and alkylaminosulfonyl.

2. The method according to claim 1 wherein the schizophrenia is chronic schizophrenic psychoses or, schizoaffective psychoses.

3. The method according to claim 1, wherein the amount of the selective COX-2 inhibitor or prodrug thereof which is administered to the subject comprises a therapeutic amount.

4. The method according to claim 1, wherein the selective COX-2 inhibitor is selected from celecoxib, rofecoxib, deracoxib, parecoxib, valdecoxib, etoricoxib, ABT-963, JTE-522, pharmaceutically acceptable salts, prodrugs and mixtures thereof.

5. The method according to claim 4, wherein the selective COX-2 inhibitor is celecoxib or a pharmaceutically acceptable salt thereof.

6. The method according to claim 5, wherein the celecoxib or a pharmaceutically acceptable salt thereof is administered to the subject in an amount of 50-1600 mg per day.

7. The method according to claim 6, wherein celecoxib or a pharmaceutically acceptable salt thereof is administered to the subject in an amount of 200-600 mg per day.

8. The method according to claim 7, wherein the celecoxib or a pharmaceutically acceptable salt thereof is administered to the subject in an amount of 400 mg per day.

9. The method according to claim 1, wherein the selective COX-2 inhibitor is administered to the subject enterally or parenterally in one or more dose per day.

10. The method according to claim 1, wherein the subject is a human.

11. A method for the treatment of schizophrenia comprising administering to a subject in need thereof an effective amount of a neuroleptic agent and a COX-2 inhibitor or prodrug thereof, wherein the selective COX-2 inhibitor is a selective COX-2 inhibitor of the following formula IV:

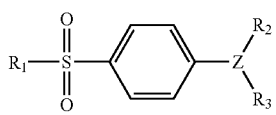

wherein
Z is selected from the group consisting of partially unsaturated or unsaturated heterocyclyl and partially unsaturated or unsaturated carbocyclic rings;
$R_1$ is selected from the group consisting of methyl or amino; and
$R_2$ is selected from the group consisting of heterocyclyl, cycloalkyl, cycloalkenyl and aryl, wherein $R_2$ is optionally substituted at a substitutable position with one or more radicals selected from alkyl, haloalkyl, cyano, carboxyl, alkoxycarbonyl, hydroxyl, hydroxyalkyl, haloalkoxy, amino, alkylamino, arylamino, nitro, alkoxyalkyl, alkylsulfinyl, halo, alkoxy and alkylthio; and
$R_3$ is selected from the group consisting of a radical selected from hydrogen, halogen, alkyl, alkenyl, alkynyl, oxygen, cyano, carboxyl, cyanoalkyl, alkyloxy, alkylthio, alkylcarbonyl, haloalkyl, alkylthioalkyl, hydroxyalkyl, alkoxycarbonyl, alkoxycarbonylalkyl, aminocarbonyl, aminocarbonylalkyl, alkylaminocarbonyl, alkylaminocarbonylalkyl, carboxyalkyl, alkylamino, aminoalkyl, alkylaminoalkyl, alkylsulfinl, alkylsulfonyl, aminosulfonyl, and alkylaminosulfonyl.

12. The method according to claim 11, wherein the amount of the neuroleptic agent and the amount of the selective COX-2 inhibitor or prodrug thereof are administered to the subject in combination and comprise a therapeutic amount of the combination.

13. The method according to claim 11 wherein the schizophrenia is chronic schizophrenic psychoses or schizoaffective psychoses.

14. The method according to claim 11, wherein the selective COX-2 inhibitor is selected from the group consisting of celecoxib, rofecoxib, ABT963, JTE-522, pharmaceutically acceptable salts, prodrugs and mixtures thereof.

15. The method according to claim 14, wherein the selective COX-2 inhibitor is celecoxib or a pharmaceutically acceptable salt thereof.

16. The method according to claim 15, wherein the celecoxib or a pharmaceutically acceptable salt thereof is administered to the subject in an amount of 50-1600 mg per day.

17. The method according to claim 16, wherein the celecoxib or a pharmaceutically acceptable salt thereof is administered to the subject in an amount of 200-600 mg per day.

18. The method according to claim 11, wherein the neuroleptic is selected from the group consisting of clozapine, olanzapine, ziprasidone, risperidone, aripiprazole, quetiapine, quetiapine fumarate, sertindole, amisulpride, haloperidol, haloperidol decanoate, haloperidol lactate, chlorpromazine, fluphenazine, fluphenazine decanoate, fluphenazine enanthate, fluphenazine hydrochloride, thiothixene, thiothixene hydrochloride, trifluoperazine, perphenazine, amitriptyline, thioridazine, mesoridazine, molindone, molindone hydrochloride, loxapine, loxapine hydrochloride, loxapine succinate, pimozide, flupenthixol, promazine, triflupromazine, chlorprothixene, droperidol, actophenazine, prochlorperazine, methotrimeprazine, pipotiazine, ziprasidone, hoperidone, zuclopenthixol, and mixtures thereof.

19. The method according to claim 18, wherein the neuroleptic is risperidone or aripiprazole.

20. The method according to claim 19, wherein the risperidone is administered to the subject in an amount of 2-6 mg per day.

21. The method according to claim 20, wherein the risperidone is administered to the subject in an amount of 4-5 mg per day.

* * * * *